US011963779B2

(12) United States Patent
Esteller

(10) Patent No.: US 11,963,779 B2
(45) Date of Patent: *Apr. 23, 2024

(54) NEUROLOGICAL EVENT DETECTION TOOLS FOR IMPLANTABLE MEDICAL DEVICES

(71) Applicant: NeuroPace, Inc., Mountain View, CA (US)

(72) Inventor: Rosana Esteller, Marietta, GA (US)

(73) Assignee: NeuroPace, Inc., Mountain View, CA (US)

( * ) Notice: Subject to any disclaimer, the term of this patent is extended or adjusted under 35 U.S.C. 154(b) by 980 days.

This patent is subject to a terminal disclaimer.

(21) Appl. No.: 16/905,644

(22) Filed: Jun. 18, 2020

(65) Prior Publication Data

US 2020/0315487 A1 Oct. 8, 2020

Related U.S. Application Data

(63) Continuation of application No. 14/828,409, filed on Aug. 17, 2015, now Pat. No. 10,729,352.

(51) Int. Cl.
*A61B 5/0478* (2006.01)
*A61B 5/00* (2006.01)
(Continued)

(52) U.S. Cl.
CPC ............... *A61B 5/291* (2021.01); *A61B 5/24* (2021.01); *A61B 5/4064* (2013.01);
(Continued)

(58) Field of Classification Search
CPC ... A61B 5/0476; A61B 5/686; A61B 5/04012; A61N 1/36082; A61N 1/36064
See application file for complete search history.

(56) References Cited

U.S. PATENT DOCUMENTS 5,047,930 A 9/1991 Martens et al.
5,280,791 A 1/1994 Peretz
(Continued)

OTHER PUBLICATIONS

Guyton, A.C., "Textbook of Medical Physiology", 8th ed., Wonsiewicz M.J. ed., pp. wii-xli (Table of Contents only), 1991.
(Continued)

*Primary Examiner* — Tse W Chen
*Assistant Examiner* — Michael A Catina
(74) *Attorney, Agent, or Firm* — LOZA & LOZA, LLP; David S. Sarisky

(57) ABSTRACT

An implantable device includes one or more electrodes to sense an electrical signal from a brain and a waveform analyzer to identify a half wave in the electrical signal; determine an amplitude and a duration of the half wave; determine if the amplitude satisfies a half wave amplitude criterion defined by a set of amplitude parameters comprising a minimum half wave amplitude and a maximum half wave amplitude; determine if the duration satisfies a half wave duration criterion defined by a set of duration parameters comprising a minimum half wave duration and a maximum half wave duration; and identify the half wave as a qualified half wave when the half wave amplitude criterion and the half wave duration criterion is satisfied. A neurological event may be detected based on one or more qualified half waves and electrical stimulation therapy may be delivered to the brain in response to the detection.

14 Claims, 19 Drawing Sheets

(51) Int. Cl.
*A61B 5/24* (2021.01)
*A61B 5/291* (2021.01)

(52) U.S. Cl.
CPC .......... *A61B 5/4094* (2013.01); *A61B 5/6868* (2013.01); *A61B 5/7282* (2013.01); *A61B 5/0006* (2013.01)

(56) References Cited

U.S. PATENT DOCUMENTS

| | | | |
|---|---|---|---|
| 5,891,176 | A | 4/1999 | Bornzin |
| 5,995,868 | A | 11/1999 | Dorfmeister |
| 6,006,124 | A | 12/1999 | Fischell et al. |
| 6,016,449 | A | 1/2000 | Fischell et al. |
| 6,473,639 | B1 | 10/2002 | Ischell et al. |
| 6,641,542 | B2 | 11/2003 | Kyun et al. |
| 6,731,984 | B2 | 5/2004 | Kyun et al. |
| 6,810,285 | B2 | 10/2004 | Pless et al. |
| 6,881,192 | B1 | 4/2005 | Park |
| 7,894,890 | B2 | 2/2011 | Sun |
| 8,068,904 | B2 | 11/2011 | Sun |
| 8,369,940 | B2 | 2/2013 | Sun |
| 8,538,514 | B2 | 9/2013 | Sun |
| 8,903,483 | B2 | 12/2014 | Sun |
| 2002/0169485 | A1 | 11/2002 | Pless et al. |
| 2005/0043652 | A1 | 2/2005 | Lovett et al. |
| 2005/0061320 | A1 | 3/2005 | Kent et al. |
| 2005/0101833 | A1 | 5/2005 | Hsu et al. |
| 2005/0148897 | A1 | 7/2005 | Cho et al. |
| 2005/0209512 | A1 | 9/2005 | Heruth et al. |
| 2005/0215847 | A1 | 9/2005 | Heruth et al. |
| 2006/0079802 | A1 | 4/2006 | Jensen et al. |
| 2006/0094972 | A1 | 5/2006 | Touby et al. |
| 2007/0213784 | A1 | 9/2007 | Pless |
| 2008/0195166 | A1 | 8/2008 | Sun et al. |
| 2008/0319335 | A1 * | 12/2008 | Greene ................ A61B 5/4094 600/544 |
| 2015/0112222 | A1 | 4/2015 | Sun |

OTHER PUBLICATIONS

Gotman, J. "Automatic Seizure Detection: Improvements and Evaluation", Electroencephalography and Clinical Neurophysiology 76(4): 317-324, (1990).

* cited by examiner

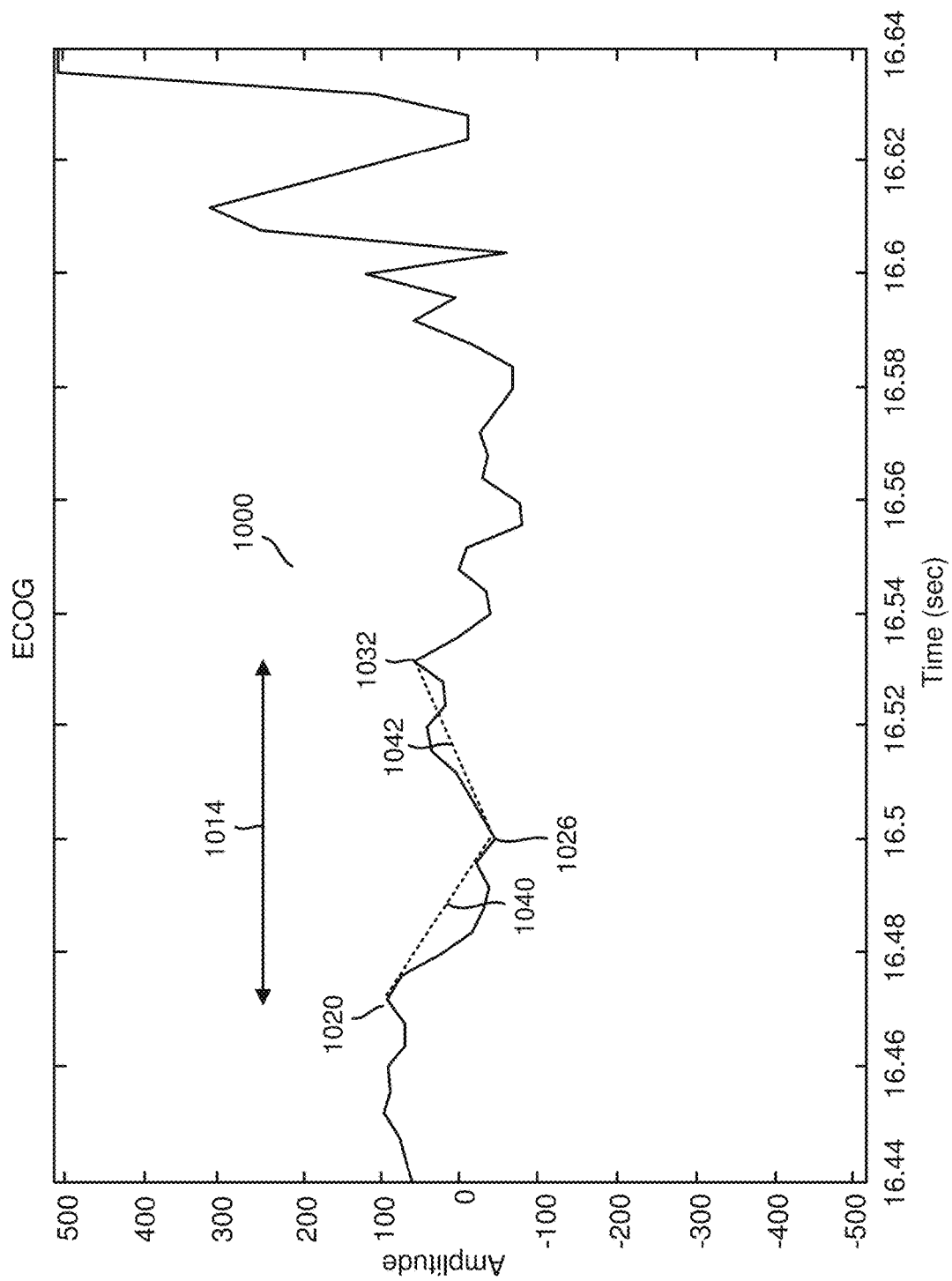

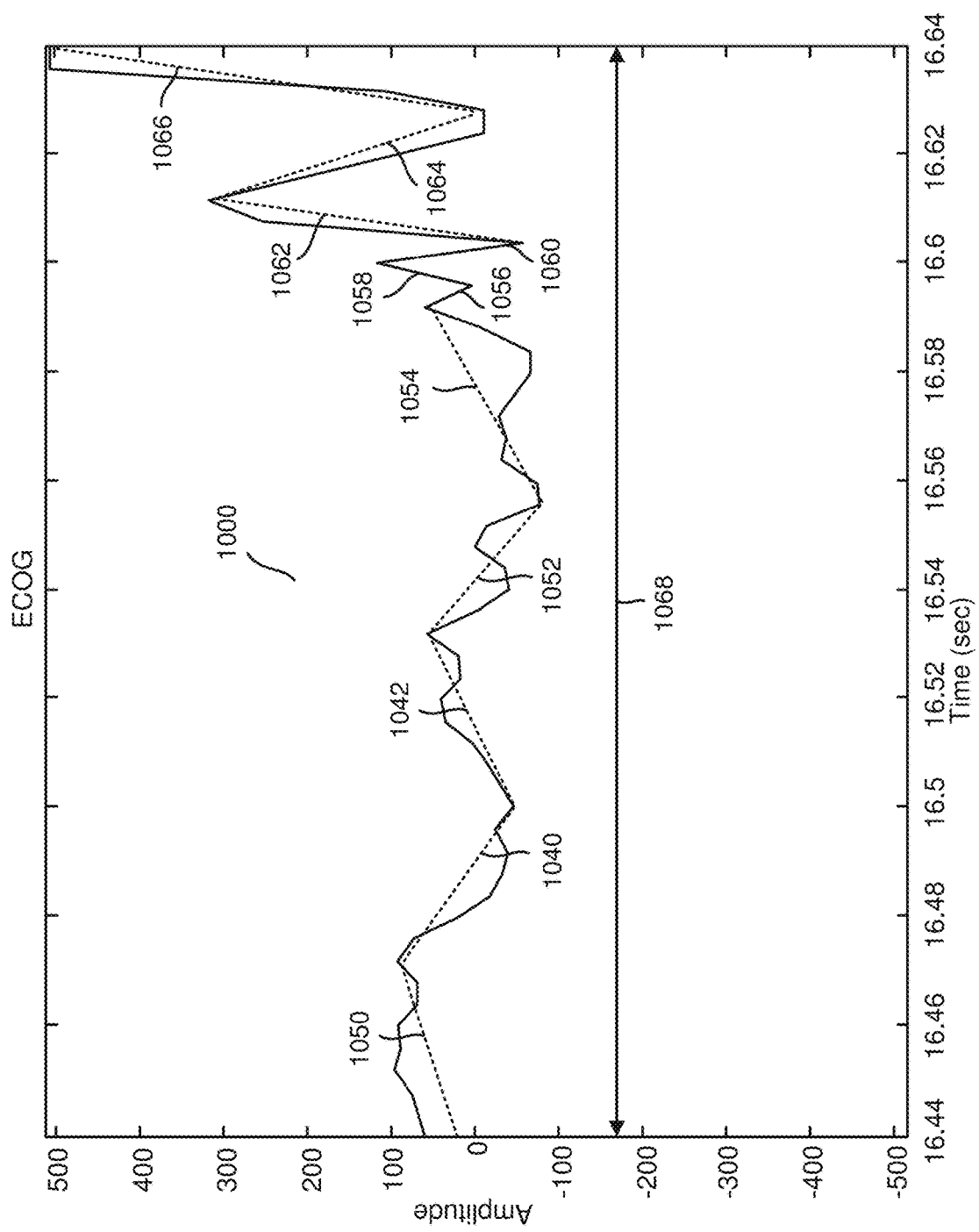

NEUROLOGICAL EVENT DETECTION TOOLS FOR IMPLANTABLE MEDICAL DEVICES

CROSS-REFERENCE TO RELATED APPLICATIONS

This application is a continuation application of U.S. patent application Ser. No. 14/828,409, filed Aug. 17, 2015, for "Neurological Event Detection Tools For Implantable Medical Devices," the entire disclosure of which is incorporated herein by reference.

TECHNICAL FIELD

The present disclosure relates to systems, devices and methods for detecting and predicting neurological dysfunction characterized by abnormal electrographic patterns, and more particularly to neurological event detection tools for implantable medical devices, where the detection tools are characterized by programmable parameters that provide for refined detection and prediction of epileptic seizures and seizure onsets by analyzing electroencephalogram (EEG) and electrocorticogram (ECoG) signals.

BACKGROUND

Epilepsy is a neurological disorder in which the nerve cell activity in the brain is disturbed, causing a seizure during which a person experiences abnormal behavior, symptoms and sensations, including for example, loss of consciousness, abnormal motor phenomena, psychic or sensory disturbances, or the perturbation of the autonomic nervous system. The episodic attacks or seizures experienced by a typical epilepsy patient are characterized by periods of abnormal neurological activity. As is traditional in the art, such periods shall be referred to herein as "ictal". "Epileptiform" activity refers to specific neurological activity associated with epilepsy as well as with an epileptic seizure and its precursors. Such activity is frequently manifested in electrographic signals in the patient's brain.

Electrical stimulation may be used to treat epilepsy. Responsive stimulation involves detecting abnormal neurological activity (e.g., ictal and epileptiform activity), determining when the detected activity represents a neurological event, and then triggering delivery of electrical stimulation when an event is detected. Implantable neurostimulators are known that use algorithms of relatively low computational complexity to detect the activity of interest and to process the information to determine whether an event should be deemed detected in order to preserve the life of the implant power source (e.g., a primary cell battery). One such algorithm involves identifying half waves in sensed EEG signals that are conditioned and processed by the implanted medical device. A so-called "half wave detector" analyzes a signal in the time domain to estimate the power of the signal in various frequency bands. U.S. Pat. No. 6,810,285 to Pless et al. for "Seizure Sensing and Detection Using an Implantable Device" describes a half wave detector that can be used alone or in combination with other forms of data analysis to decide whether an event has occurred that merits triggering a form of electrical stimulation in response. U.S. Pat. No. 6,810,285 is incorporated herein in the entirety by reference. In general, the signals of interest represent aggregate neuronal activity potentials (local field potentials or LFPs) detectable via electrodes. When the electrodes are applied to a patient's scalp, the signals acquired are usually referred to as an EEG. When the electrodes are applied intracranially, such as placed on or near the surface of the brain (e.g., on or near the dura mater) or within the brain (e.g., via depth electrodes), the signals acquired may be referred to as an ECoG (electrocorticogram) or ECoGs (electrocorticographic signals) . . . . Unless the context clearly and expressly indicates otherwise, the term "EEG" shall be used generically herein to refer to both EEG and ECoG signals. Responsive stimulation involves the application of electrical stimulation in response to detection of epileptiform activity.

Other approaches to analyzing EEG signals involve transforming them into the frequency domain for rigorous spectrum analysis. See, e.g., U.S. Pat. No. 5,995,868 to Dorfineister et al., which analyzes the power spectral density of EEG signals in comparison to background characteristics. Although such approaches generally are believed to achieve good results, for the most part, they can be more computationally expensive than time domain analyses, making them less attractive for use in an implant that is intended to be implanted chronically. Whenever the analysis is being carried out in an implantable device, the real estate and power required to implement it is always an important design consideration. All of these approaches provide useful information, and in some cases may provide sufficient information for accurate detection and prediction of most imminent epileptic seizures. However, none of the various implementations of the known approaches provide 100% seizure detection accuracy in a clinical environment.

With any analysis, an objective is to avoid detection errors such as false positives and false negatives. A "false positive" refers to a detection of an ictal or epileptiform activity when no such abnormal activity is actually occurring. A "false negative" refers to the failure to detect abnormal activity when it is, in fact, occurring or, in some circumstances, when it is about to occur.

Detection tools or algorithms often can be tailored or tuned to detect activity that is abnormal for a particular patient: What is abnormal for one patient may be different than what is abnormal for another. Ideally, a detection algorithm would be tunable to capture all of the abnormal activity of interest and nothing that is not abnormal, that is, no false negatives and no false positives. A detection algorithm that results in no false positives and no false negatives may be described as having 100% specificity (no false positives) and 100% sensitivity (no false negatives). However, it is likely that when a detection algorithm is tuned to catch all of the abnormal activity (e.g., ictal and epileptiform), there will be a significant number of false positives. When the results of a detection algorithm determine when stimulation is delivered to the patient, it of course is desirable to minimize false positives, so that the patient is not being stimulated unless the abnormal activity of interest is occurring. Similarly, it is desirable not to miss any instances of the activity of interest and thus an objective with any detection algorithm is to avoid false negatives.

Thus, there is a need for an implantable device that can detect events in EEG activity that correlate to abnormal neurological activity in a more refined manner relative to existing techniques, without excessive computational complexity but nevertheless with a controllably low rate of false positives and/or false negatives.

SUMMARY

An implantable medical device includes a waveform analyzer that may be tuned or tailored through programmable parameters to provide for more sensitive (low rate of false negatives) and more specific (low rate false positives) detection of abnormal neurological activity, e.g., ictal or epileptiform activity, relative to known waveform analyzers. The waveform analyzer is tuned or tailored by additional programmable parameters not present in known implantable medical devices. These additional parameters provide for improved processing of electrographic signals and identification of particular signal characteristics, e.g., low fast frequency activity, gamma activity, spike activity, within such signals through the detection and classification of qualified half waves. The improved processing and identification of signal characteristics in turn provides for an implantable medical device with an improved neurological event detection tool that may detect fewer false positives and avoid false negatives, in a computationally and power efficient manner.

The improved implantable medical device includes one or more electrodes configured to sense an electrical signal from a patient's brain and a waveform analyzer. The waveform analyzer is configured to identify a half wave in the electrical signal and to determine an amplitude of the half wave and a duration of the half wave. The waveform analyzer is characterized by a set of amplitude parameters and a set of duration parameters that are used to determine whether an identified half wave meets criteria so as to be classified as a qualified half wave. While existing waveform analyzers may be tuned or tailored to detect qualified half waves based on a minimum half wave amplitude and a minimum half wave duration, waveform analyzers configured in accordance with embodiments disclosed herein, include additional parameters.

In one embodiment, the set of amplitude parameters include a minimum half wave amplitude and a maximum half wave amplitude, and the set of duration parameters include a minimum half wave duration and a maximum half wave duration. The additional two parameters (maximum half wave amplitude and maximum half wave duration), in combination with existing minimum half wave amplitude and a minimum half wave duration parameters, characterize a four-parameter implementation of a half wave detection tool that may be tuned to provide for identification of electrographic signal characteristics and corresponding neurological event detections in a more sensitive and specific fashion.

In another embodiment, the set of amplitude parameters include a minimum half wave amplitude and a maximum half wave amplitude for each of positive slope half waves and negative slope half waves, and the set of duration parameters include a minimum half wave duration and a maximum half wave duration for each of positive slope half waves and negative slope half waves. The combination of positive slope parameters and negative slope parameters characterize an eight-parameter implementation of a half wave detection tool that may be tuned provide for identification of electrographic signal characteristics and corresponding neurological event detections in a more sensitive and specific fashion.

Based on these respective parameters, the waveform analyzer determines if the amplitude of the half wave satisfies a half wave amplitude criterion defined by the set of amplitude parameters, and if the duration of the half wave satisfies a half wave duration criterion defined by the set of duration parameters. The waveform analyzer identifies the half wave as a qualified half wave when both of the half wave amplitude criterion and half wave duration criterion are satisfied. Qualified half waves are further processed to determine if a neurological event, e.g., abnormal neurological activity, is detected. The abnormal neurological activity may be ictal or epileptiform activity indicative of an epileptic seizure or an onset thereof.

BRIEF DESCRIPTION OF THE DRAWINGS

Aspects, features, benefits and advantages of the embodiments described herein will be apparent with regard to the following description, appended claims and accompanying drawings where:

FIG. 10B is the graph of FIG. 10A in which two half waves are identified.

FIG. 10C is the graph of FIG. 10A in which a set of eleven half waves are identified.

DETAILED DESCRIPTION

Embodiments disclosed herein relate to systems, devices and methods for detecting and predicting neurological dysfunction characterized by abnormal electrographic patterns, including detecting and predicting epileptic seizures and their onsets by analyzing EEG and ECoG signals with an implantable device.

Neurostimulation System

Figure 1:
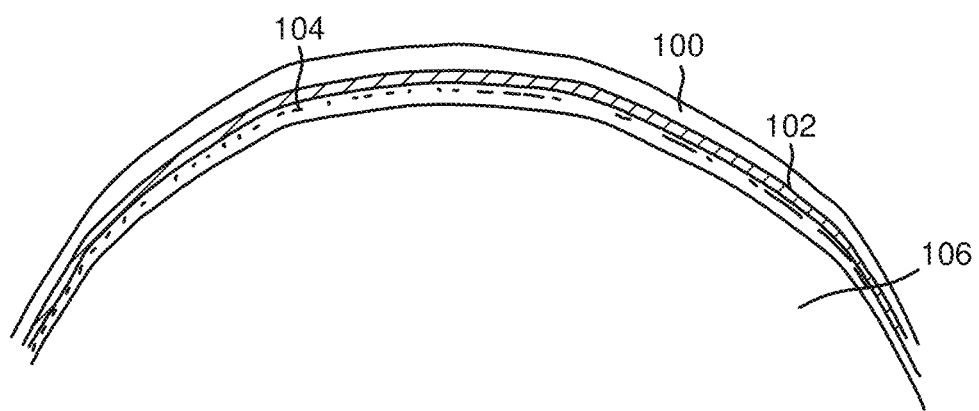
FIG. 1 is a schematic illustration of a patient's head showing the placement of an implantable neurostimulator according to an embodiment of the invention.

FIG. 1 depicts an intracranially implanted device 110 according to the invention, which in one embodiment is a small self-contained responsive neurostimulator. As the term is used herein, a responsive neurostimulator is a device capable of detecting or predicting ictal or epileptiform activity (or other neurological events) and providing electrical stimulation to neural tissue in response to that activity, where the electrical stimulation is specifically intended to terminate the abnormal activity, treat a neurological event, prevent an unwanted neurological event from occurring, or lessen the severity or frequency of certain symptoms of a neurological disorder. As disclosed herein, the responsive neurostimulator detects the activity of interest by systems and methods according to the invention.

Preferably, an implantable device according to the invention is capable of detecting or predicting any kind of neurological event that has a representative electrographic signature. While the disclosed embodiment is described primarily as responsive to epileptic seizures, it should be recognized that it is also possible to respond to other types of neurological disorders, such as movement disorders (e.g. the tremors characterizing Parkinson's disease), migraine headaches, chronic pain, and neuropsychiatric disorders such as depression. Preferably, neurological events representing any or all of these afflictions can be detected when they are actually occurring, in an onset stage, or as a predictive precursor before clinical symptoms begin.

Figure 2:
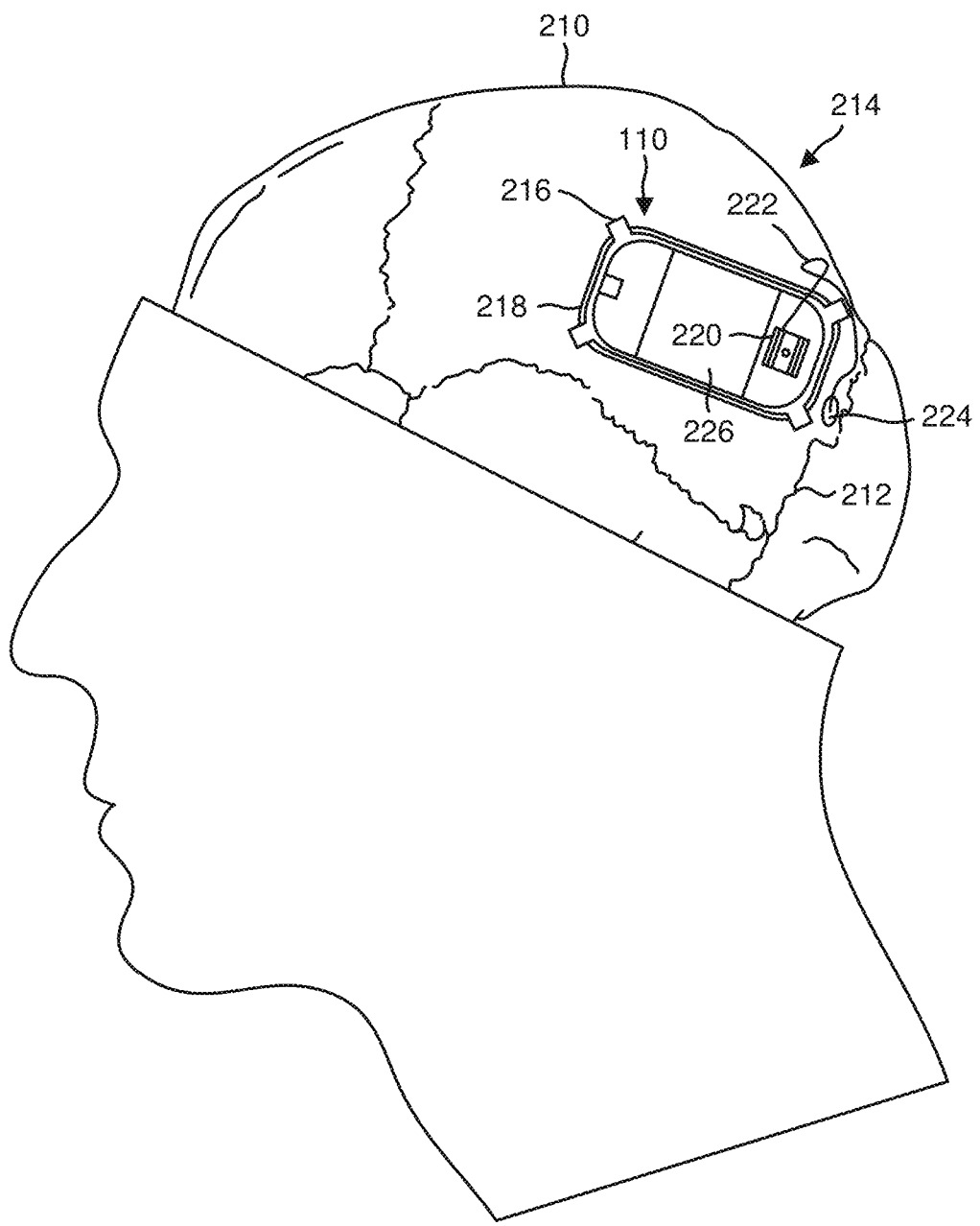
FIG. 2 is a schematic illustration of a patient's cranium showing the implantable neurostimulator of FIG. 1 as implanted, including leads extending to the patient's brain.

In the disclosed embodiment, the neurostimulator is implanted intracranially in a patient's parietal bone 210, in a location anterior to the lambdoidal suture 212 (see FIG. 2). It should be noted, however, that the placement described and illustrated herein is merely exemplary, and other locations and configurations are also possible, in the cranium or elsewhere, depending on the size and shape of the device and individual patient needs, among other factors. The device 110 is preferably configured to fit the contours of the patient's cranium 214. In an alternative embodiment, the device 110 is implanted under the patient's scalp 112 but external to the cranium; it is expected, however, that this configuration would generally cause an undesirable protrusion in the patient's scalp where the device is located. In yet another alternative embodiment, when it is not possible to implant the device intracranially, it may be implanted pectorally (not shown), with leads extending through the patient's neck and between the patient's cranium and scalp, as necessary.

It should be recognized that the embodiment of the device 110 described and illustrated herein is preferably a responsive neurostimulator for detecting and treating epilepsy by detecting seizures or their onsets or precursors, and preventing and/or terminating such epileptic seizures.

In an alternative embodiment of the invention, the device 110 is not a responsive neurostimulator, but is an apparatus capable of detecting neurological conditions and events and performing actions in response thereto. The actions performed by such an embodiment of the device 110 need not be therapeutic, but may involve data recording or transmission, providing warnings to the patient, or any of a number of known alternative actions. Such a device will typically act as a diagnostic device when interfaced with external equipment, as will be discussed in further detail below.

The device 110, as implanted intracranially, is illustrated in greater detail in FIG. 2. The device 110 is affixed in the patient's cranium 214 by way of a ferrule 216. The ferrule 216 is a structural member adapted to fit into a cranial opening, attach to the cranium 214, and retain the device 110.

To implant the device 110, a craniotomy is performed in the parietal bone anterior to the lambdoidal suture 212 to define an opening 218 slightly larger than the device 110. The ferrule 216 is inserted into the opening 218 and affixed to the cranium 214, ensuring a tight and secure fit. The device 110 is then inserted into and affixed to the ferrule 216.

As shown in FIG. 2, the device 110 includes a lead connector 220 adapted to receive one or more electrical leads, such as a first lead 222. The lead connector 220 acts to physically secure the lead 222 to the device 110, and facilitates electrical connection between a conductor in the lead 222 coupling an electrode to circuitry within the device 110. The lead connector 220 accomplishes this in a substantially fluid-tight environment with biocompatible materials.

The lead 222, as illustrated, and other leads for use in a system or method according to the invention, is a flexible elongated member having one or more conductors. As shown, the lead 222 is coupled to the device 110 via the lead connector 220, and is generally situated on the outer surface of the cranium 214 (and under the patient's scalp 112), extending between the device 110 and a burr hole 224 or other cranial opening, where the lead 222 enters the cranium 214 and is coupled to a depth electrode (see FIG. 4) implanted in a desired location in the patient's brain. If the length of the lead 222 is substantially greater than the distance between the device 110 and the burr hole 224, any excess may be urged into a coil configuration under the scalp 112. As described in U.S. Pat. No. 6,006,124 for "Means and Method for the Placement of Brain Electrodes" to Fischell, et al., which is hereby incorporated by reference as though set forth in full herein, the burr hole 224 is sealed after implantation to prevent further movement of the lead 222; in an embodiment of the invention, a burr hole cover apparatus is affixed to the cranium 214 at least partially within the burr hole 224 to provide this functionality.

The device 110 includes a durable outer housing 226 fabricated from a biocompatible material. Titanium, which is light, extremely strong, and biocompatible, is used in analogous devices, such as cardiac pacemakers, and would serve advantageously in this context. As the device 110 is self-contained, the housing 226 encloses a battery and any electronic circuitry necessary or desirable to provide the functionality described herein, as well as any other features. As will be described in further detail below, a telemetry coil may be provided outside of the housing 226 (and potentially integrated with the lead connector 220) to facilitate communication between the device 110 and external devices.

The neurostimulator configuration described herein and illustrated in FIG. 2 provides several advantages over alternative designs. First, the self-contained nature of the neurostimulator substantially decreases the need for access to the device 110, allowing the patient to participate in normal life activities. Its small size and intracranial placement causes a minimum of cosmetic disfigurement. The device 110 will fit in an opening in the patient's cranium, under the patient's scalp, with little noticeable protrusion or bulge. The ferrule 216 used for implantation allows the craniotomy to be performed and fit verified without the possibility of breaking the device 110, and also provides protection against the device 110 being pushed into the brain under external pressure or impact. A further advantage is that the ferrule 216 receives any cranial bone growth, so at explant, the device 110 can be replaced without removing any bone screws—only the fasteners retaining the device 110 in the ferrule 216 need be manipulated.

Figure 3:
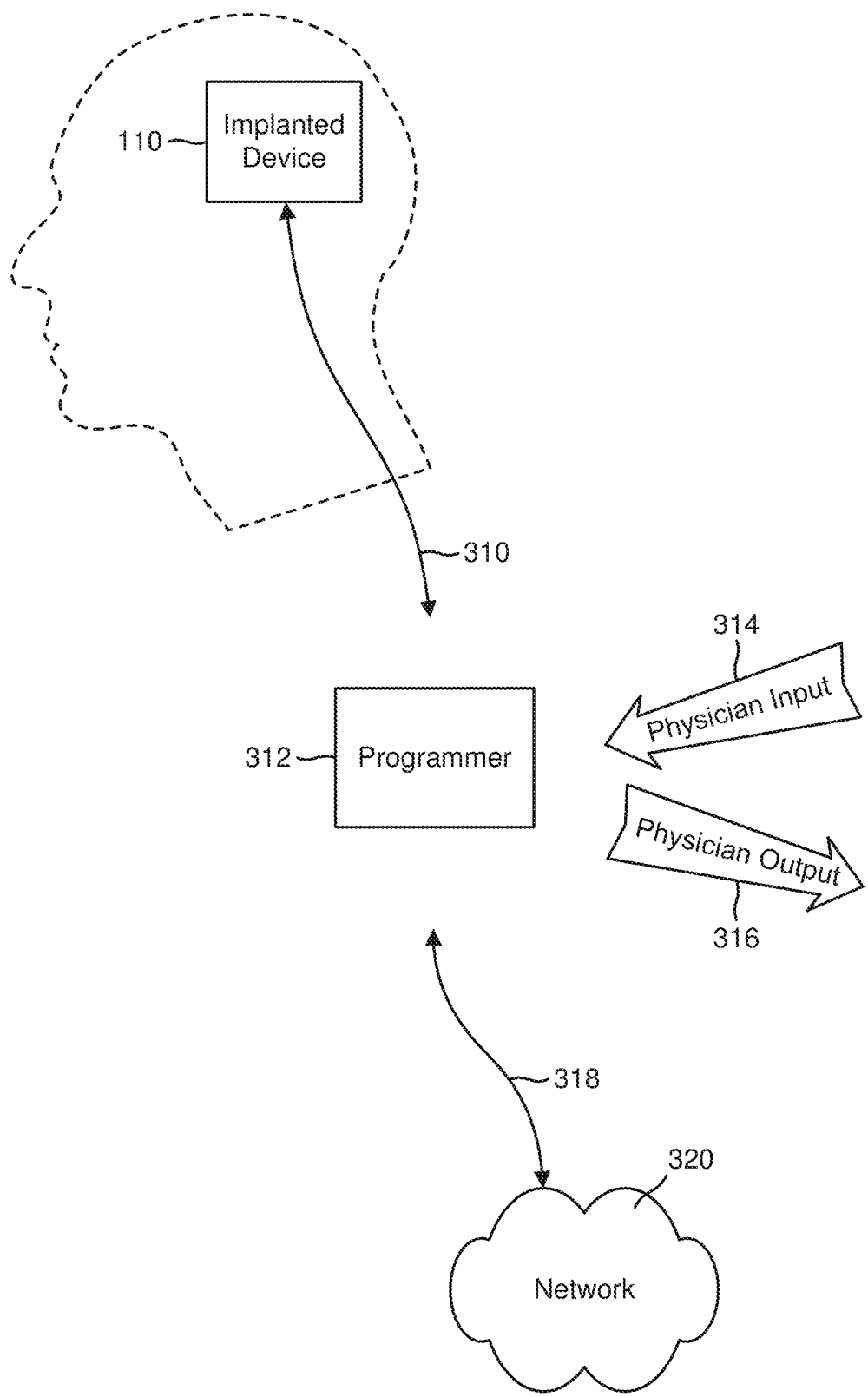
FIG. 3 is a block diagram illustrating context in which an implantable neurostimulator according to the invention is implanted and operated.

As stated above, and as illustrated in FIG. 3, a neurostimulator according to the invention operates in conjunction with external equipment. The device 110 is mostly autonomous (particularly when performing its usual sensing, detection, and stimulation capabilities), but preferably includes a selectable part-time wireless link 310 to external equipment such as a programmer 312. In the disclosed embodiment of the invention, the wireless link 310 is established by moving a wand (or other apparatus) having communication capabilities and coupled to the programmer 312 into range of the device 110. The programmer 312 can then be used to manually control the operation of the device 110, as well as to transmit information to or receive information from the device 110. Several specific capabilities and operations performed by the programmer 312 in conjunction with the device 110 will be described in further detail below.

The programmer 312 is capable of performing a number of advantageous operations in connection with the invention. In particular, the programmer 312 is able to specify and set variable parameters in the device 110 to adapt the function of the device 110 to meet the patient's needs, download or receive data (including but not limited to stored EEG waveforms, parameters, or logs of actions taken) from the device 110 to the programmer 312, upload or transmit program code and other information from the programmer 312 to the device 110, or command the device 110 to perform specific actions or change modes as desired by a physician operating the programmer 312. To facilitate these functions, the programmer 312 is adapted to receive physician input 314 and provide physician output 316; data is transmitted between the programmer 312 and the device 110 over the wireless link 310.

The programmer 312 may be coupled via a communication link 318 to a network 320 such as the Internet. This allows any information downloaded from the device 110, as well as any program code or other information to be uploaded to the device 110, to be stored in a database at one or more data repository locations (which may include various servers and network-connected programmers like the programmer 312). This would allow a patient (and the patient's physician) to have access to important data, including past treatment information and software updates, essentially anywhere in the world that there is a programmer (like the programmer 312) and a network connection.

Figure 4:
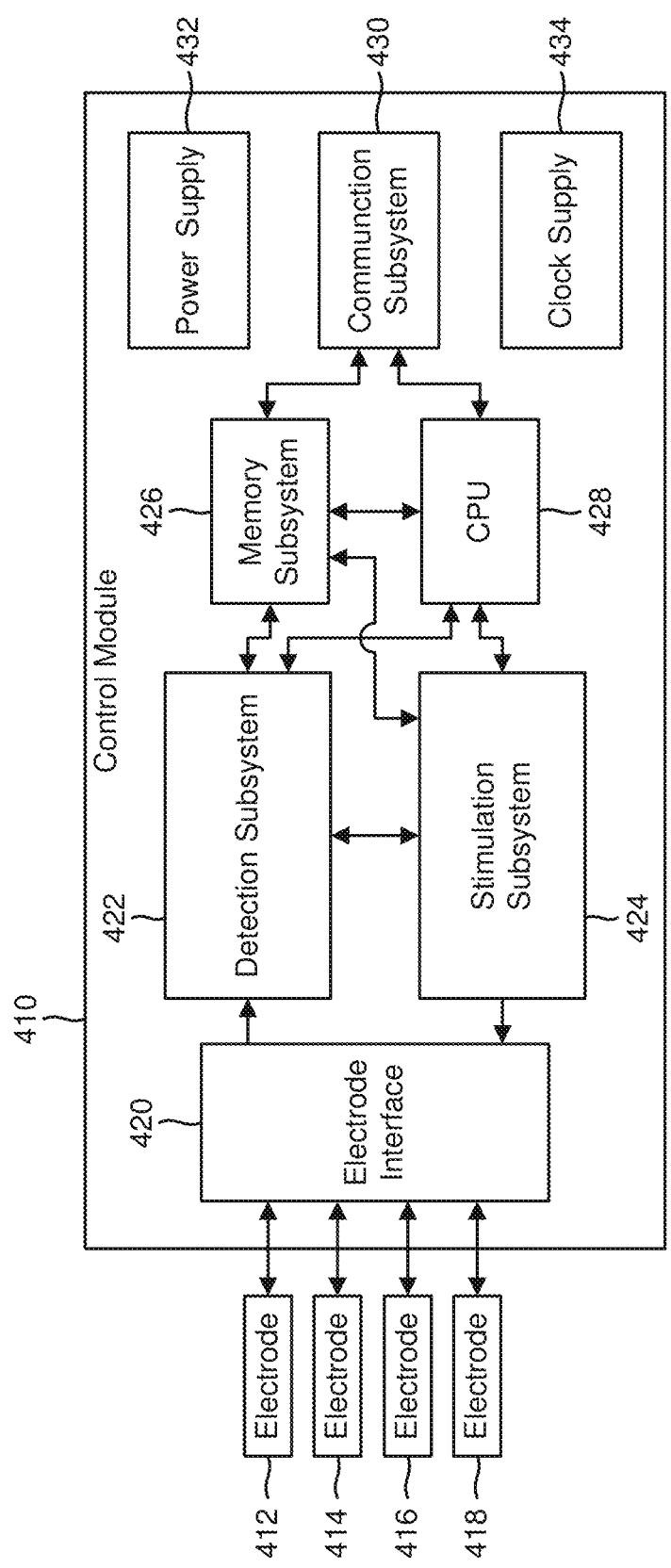
FIG. 4 is a block diagram illustrating the major functional subsystems of an implantable neurostimulator according to the invention.

An overall block diagram of the device 110 used for measurement, detection, and treatment according to the invention is illustrated in FIG. 4. Inside the housing 226 of the device 110 are several subsystems making up a control module 410. The control module 410 is capable of being coupled to a plurality of electrodes 412, 414, 416, and 418 (each of which may be connected to the control module 410 via a lead that is analogous or identical to the lead 222 of FIG. 2) for sensing and stimulation. In the illustrated embodiment, the coupling is accomplished through the lead connector 220 (FIG. 2). Although four electrodes are shown in FIG. 4, it should be recognized that any number is possible, and in the embodiment described in detail below, eight electrodes are used. In fact, it is possible to employ an embodiment of the invention that uses a single lead with at least two electrodes, or two leads each with a single electrode (or with a second electrode provided by a conductive exterior portion of the housing 226 in one embodiment), although bipolar sensing between two closely spaced electrodes on a lead is preferred to minimize common mode signals including noise.

The electrodes 412-418 are connected to an electrode interface 420. Preferably, the electrode interface is capable of selecting each electrode as required for sensing and stimulation; accordingly the electrode interface is coupled to a detection subsystem 422 and a stimulation subsystem 424. The electrode interface also may provide any other features, capabilities, or aspects, including but not limited to amplification, isolation, and charge-balancing functions, that are required for a proper interface with neurological tissue and not provided by any other subsystem of the device 110.

The detection subsystem 422 includes an EEG analyzer function. The EEG analyzer function is adapted to receive EEG signals from the electrodes 412-418, through the electrode interface 420, and to process those EEG signals to identify neurological activity indicative of a seizure, an onset of a seizure, or a precursor to a seizure. One way to implement such EEG analysis functionality is disclosed in detail in U.S. Pat. No. 6,016,449 for "System for Treatment of Neurological Disorders" to Fischell et al., incorporated by reference above; additional inventive methods are described in detail below. The detection subsystem may optionally also contain further sensing and detection capabilities, including but not limited to parameters derived from other physiological conditions (such as electrophysiological parameters, temperature, blood pressure, etc.).

The stimulation subsystem 424 is capable of applying electrical stimulation to neurological tissue through the electrodes 412-418. This can be accomplished in any of a number of different manners. For example, it may be advantageous in some circumstances to provide stimulation in the form of a substantially continuous stream of pulses, or on a scheduled basis. Preferably, therapeutic stimulation is provided in response to abnormal events detected by the EEG analyzer function of the detection subsystem 422. As illustrated in FIG. 4, the stimulation subsystem 424 and the EEG analyzer function of the detection subsystem 422 are in communication; this facilitates the ability of stimulation subsystem 424 to provide responsive stimulation as well as an ability of the detection subsystem 422 to blank the amplifiers while stimulation is being performed to minimize stimulation artifacts. It is contemplated that the parameters of the stimulation signal (e.g., frequency, duration, waveform) provided by the stimulation subsystem 424 would be specified by other subsystems in the control module 410, as will be described in further detail below.

Also in the control module 410 is a memory subsystem 426 and a central processing unit (CPU) 428, which can take the form of a microcontroller. The memory subsystem is coupled to the detection subsystem 422 (e.g., for receiving and storing data representative of sensed EEG signals and evoked responses), the stimulation subsystem 424 (e.g., for providing stimulation waveform parameters to the stimulation subsystem), and the CPU 428, which can control the operation of the memory subsystem 426. In addition to the memory subsystem 426, the CPU 428 is also connected to the detection subsystem 422 and the stimulation subsystem 424 for direct control of those subsystems.

Also provided in the control module 410, and coupled to the memory subsystem 426 and the CPU 428, is a communication subsystem 430. The communication subsystem 430 enables communication between the device 110 (FIG. 1) and the outside world, particularly the external programmer 312 (FIG. 3). As set forth above, the disclosed embodiment of the communication subsystem 430 includes a telemetry coil (which may be situated outside of the housing 226) enabling transmission and reception of signals, to or from an external apparatus, via inductive coupling. Alternative embodiments of the communication subsystem 430 could use an antenna for an RF link or an audio transducer for an audio link.

Rounding out the subsystems in the control module 410 are a power supply 432 and a clock supply 434. The power supply 432 supplies the voltages and currents necessary for each of the other subsystems. The clock supply 434 supplies substantially all of the other subsystems with any clock and timing signals necessary for their operation.

It should be observed that while the memory subsystem 426 is illustrated in FIG. 4 as a separate functional subsystem, the other subsystems may also require various amounts of memory to perform the functions described above and others. Furthermore, while the control module 410 is preferably a single physical unit contained within a single physical enclosure, namely the housing 226 (FIG. 2), it may comprise a plurality of spatially separate units each performing a subset of the capabilities described above. Also, it should be noted that the various functions and capabilities of the subsystems described above may be performed by electronic hardware, computer software (or firmware), or a combination thereof. The division of work between the CPU 428 and the other functional subsystems may also vary—the functional distinctions illustrated in FIG. 4 may not reflect the integration of functions in a real-world system or method according to the invention.

Figure 5:
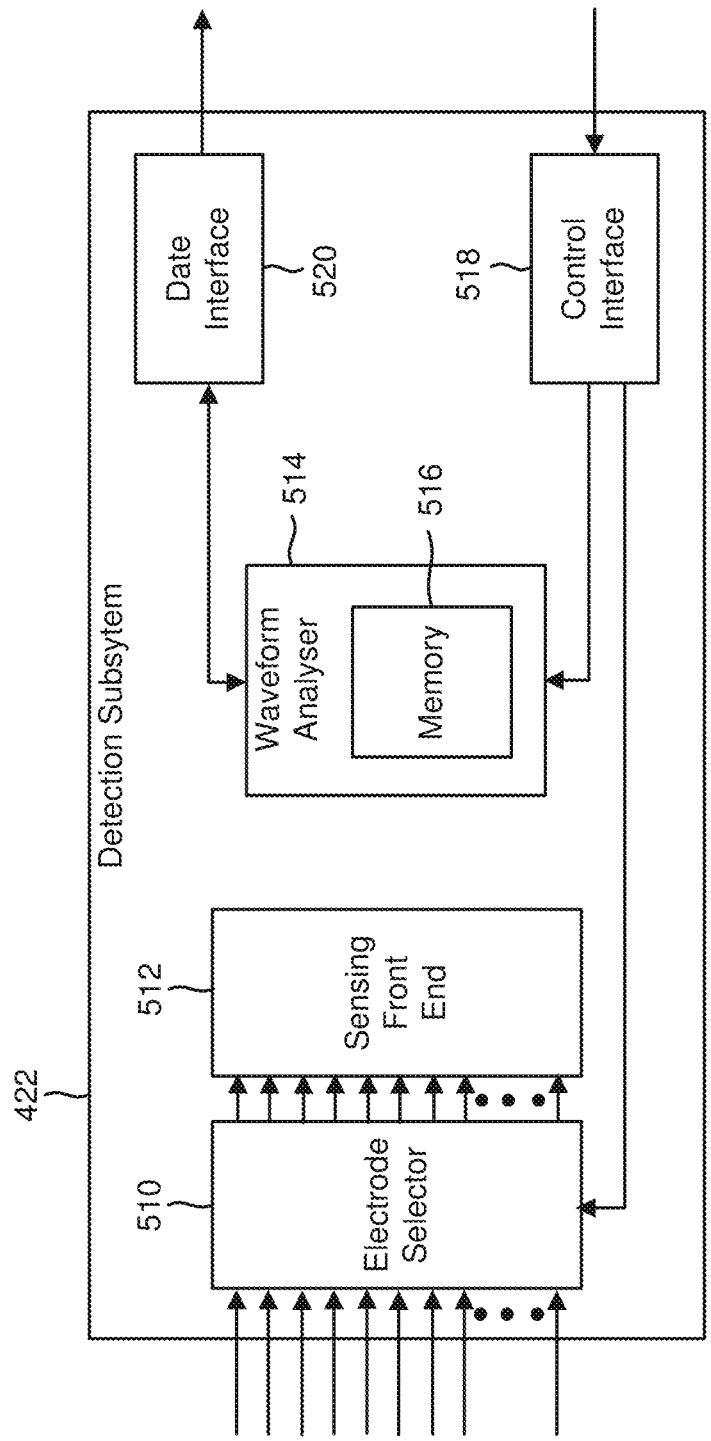
FIG. 5 is a block diagram illustrating the functional components of the detection subsystem of the implantable neurostimulator shown in FIG. 4.

FIG. 5 illustrates details of the detection subsystem 422 (FIG. 4). Inputs from the electrodes 412-418 are on the left, and connections to other subsystems are on the right.

Signals received from the electrodes 412-418 (as routed through the electrode interface 420) are received in an electrode selector 510. The electrode selector 510 allows the device to select which electrodes (of the electrodes 412-418) should be routed to which individual sensing channels of the detection subsystem 422, based on commands received through a control interface 518 from the memory subsystem 426 or the CPU 428 (FIG. 4). Preferably, each sensing channel of the detection subsystem 422 receives a bipolar signal representative of the difference in electrical potential between two selectable electrodes. Accordingly, the electrode selector 510 provides signals corresponding to each pair of selected electrodes (of the electrodes 412-418) to a sensing front end 512, which performs amplification, analog to digital conversion, and multiplexing functions on the signals in the sensing channels. The sensing front end will be described further below in connection with FIG. 6.

A multiplexed input signal representative of all active sensing channels is then fed from the sensing front end 512 to a waveform analyzer 514. The waveform analyzer 514 is preferably a special-purpose digital signal processor (DSP) adapted for use with the invention, or in an alternative embodiment, may comprise a programmable general-purpose DSP. In the disclosed embodiment, the waveform analyzer has its own scratchpad memory area 516 used for local storage of data and program variables when the signal processing is being performed. In either case, the signal processor performs suitable measurement and detection methods described generally above and in greater detail below. Any results from such methods, as well as any digitized signals intended for storage transmission to external equipment, are passed to various other subsystems of the control module 410, including the memory subsystem 426 and the CPU 428 (FIG. 4) through a data interface 520. Similarly, the control interface 518 allows the waveform analyzer 514 and the electrode selector 510 to be in communication with the CPU 428.

Figure 6:
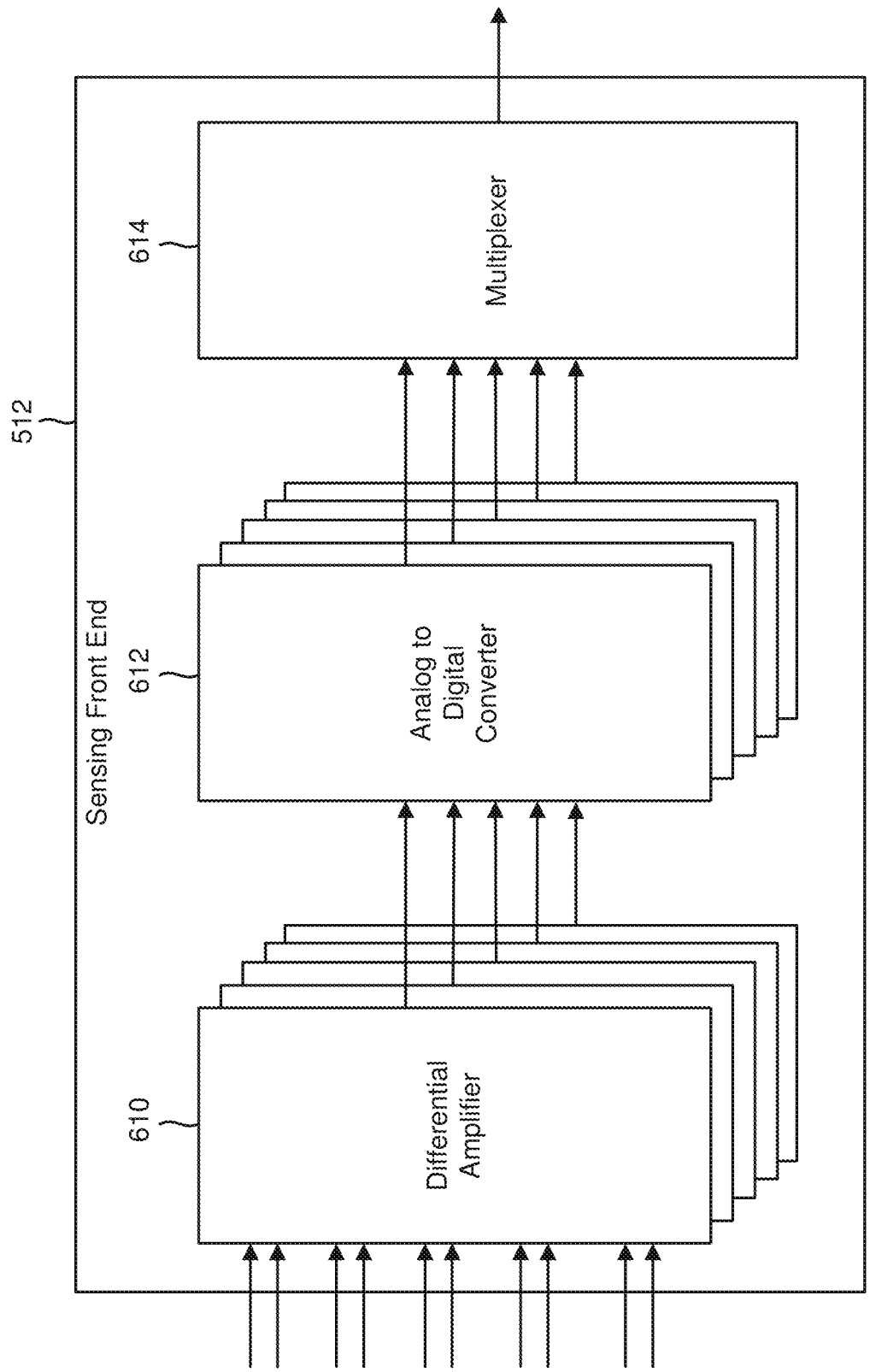
FIG. 6 is a block diagram illustrating the functional components of the sensing front end of the detection subsystem of FIG. 5.

Referring now to FIG. 6, the sensing front end 512 (FIG. 5) is illustrated in further detail. As shown, the sensing front end includes a plurality of differential amplifier channels 610, each of which receives a selected pair of inputs from the electrode selector 510. In a preferred embodiment of the invention, each of differential amplifier channels 610 is adapted to receive or to share inputs with one or more other differential amplifier channels 610 without adversely affecting the sensing and detection capabilities of a system according to the invention. Specifically, in an embodiment of the invention, there are at least eight electrodes, which can be mapped separately to eight differential amplifier channels 610 representing eight different sensing channels and capable of individually processing eight bipolar signals, each of which represents an electrical potential difference between two monopolar input signals received from the electrodes and applied to the sensing channels via the electrode selector 510. For clarity, only five channels are illustrated in FIG. 6, but it should be noted that any practical number of sensing channels may be employed in a system according to the invention.

Each differential amplifier channel 610 feeds a corresponding analog to digital converter (ADC) 612. Preferably, the analog to digital converters 612 are separately programmable with respect to sample rates—in the disclosed embodiment, the ADCs 612 convert analog signals into 10-bit unsigned integer digital data streams at a sample rate selectable between 250 Hz and 500 Hz. In several of the illustrations described below where waveforms are shown, sample rates of 250 Hz are typically used for simplicity. However, the invention shall not be deemed to be so limited, and numerous sample rate and resolution options are possible, with tradeoffs known to individuals of ordinary skill in the art of electronic signal processing. The resulting digital signals are received by a multiplexer 614 that creates a single interleaved digital data stream representative of the data from all active sensing channels. As will be described in further detail below, not all of the sensing channels need to be used at one time, and it may in fact be advantageous in certain circumstances to deactivate certain sensing channels to reduce the power consumed by a system according to the invention.

It should be noted that as illustrated and described herein, a "sensing channel" is not necessarily a single physical or functional item that can be identified in any illustration. Rather, a sensing channel is formed from the functional sequence of operations described herein, and particularly represents a single electrical signal received from any pair or combination of electrodes, as preprocessed by a system according to the invention, in both analog and digital forms. See, e.g., U.S. Pat. No. 6,473,639 to D. Fischell et al., filed on Mar. 2, 2000 and entitled "Neurological Event Detection Using Processed Display Channel Based Algorithms and Devices Incorporating These Procedures," which is hereby incorporated by reference as though set forth in full herein. At times (particularly after the multiplexer 614), multiple sensing channels are processed by the same physical and functional components of the system; notwithstanding that, it should be recognized that unless the description herein indicates to the contrary, a system according to the invention processes, handles, and treats each sensing channel independently.

The interleaved digital data stream is passed from the multiplexer 614, out of the sensing front end 512, and into the waveform analyzer 514. The waveform analyzer 514 is illustrated in detail in FIG. 7.

The interleaved digital data stream representing information from all of the active sensing channels is first received by a channel controller 710. The channel controller applies information from the active sensing channels to a number of wave morphology analysis units 712 and window analysis units 714. It is preferred to have as many wave morphology analysis units 712 and window analysis units 714 as possible, consistent with the goals of efficiency, size, and low power consumption necessary for an implantable device. In a presently preferred embodiment of the invention, there are sixteen wave morphology analysis units 712 and eight window analysis units 714, each of which can receive data from any of the sensing channels of the sensing front end 512, and each of which can be operated with different and independent parameters, including differing sample rates, as will be discussed in further detail below.

Each of the wave morphology analysis units 712 operates to extract certain feature information from an input waveform as described below in conjunction with FIGS. 9-11. Each of the window analysis units 714 performs certain data reduction and signal analysis within time windows in the manner described in U.S. Pat. No. 6,810,285, previously incorporated by reference. Output data from the various wave morphology analysis units 712 and window analysis units 714 are combined via event detector logic 716. The event detector logic 716 and the channel controller 710 are controlled by control commands 718 received from the control interface 518 (FIG. 5).

A "detection channel," as the term is used herein, refers to a data stream including the active sensing front end 512 and the analysis units of the waveform analyzer 514 processing that data stream, in both analog and digital forms. It should be noted that each detection channel can receive data from a single sensing channel; each sensing channel preferably can be applied to the input of any combination of detection channels. The latter selection is accomplished by the channel controller 710. As with the sensing channels, not all detection channels need to be active; certain detection channels can be deactivated to save power or if additional detection processing is deemed unnecessary in certain applications.

In conjunction with the operation of the wave morphology analysis units 712 and the window analysis units 714, a scratchpad memory area 516 is provided for temporary storage of processed data. The scratchpad memory area 516 may be physically part of the memory subsystem 426, or alternatively may be provided for the exclusive use of the waveform analyzer 514. Other subsystems and components of a system according to the invention may also be furnished with local scratchpad memory, if such a configuration is advantageous.

Figure 8:
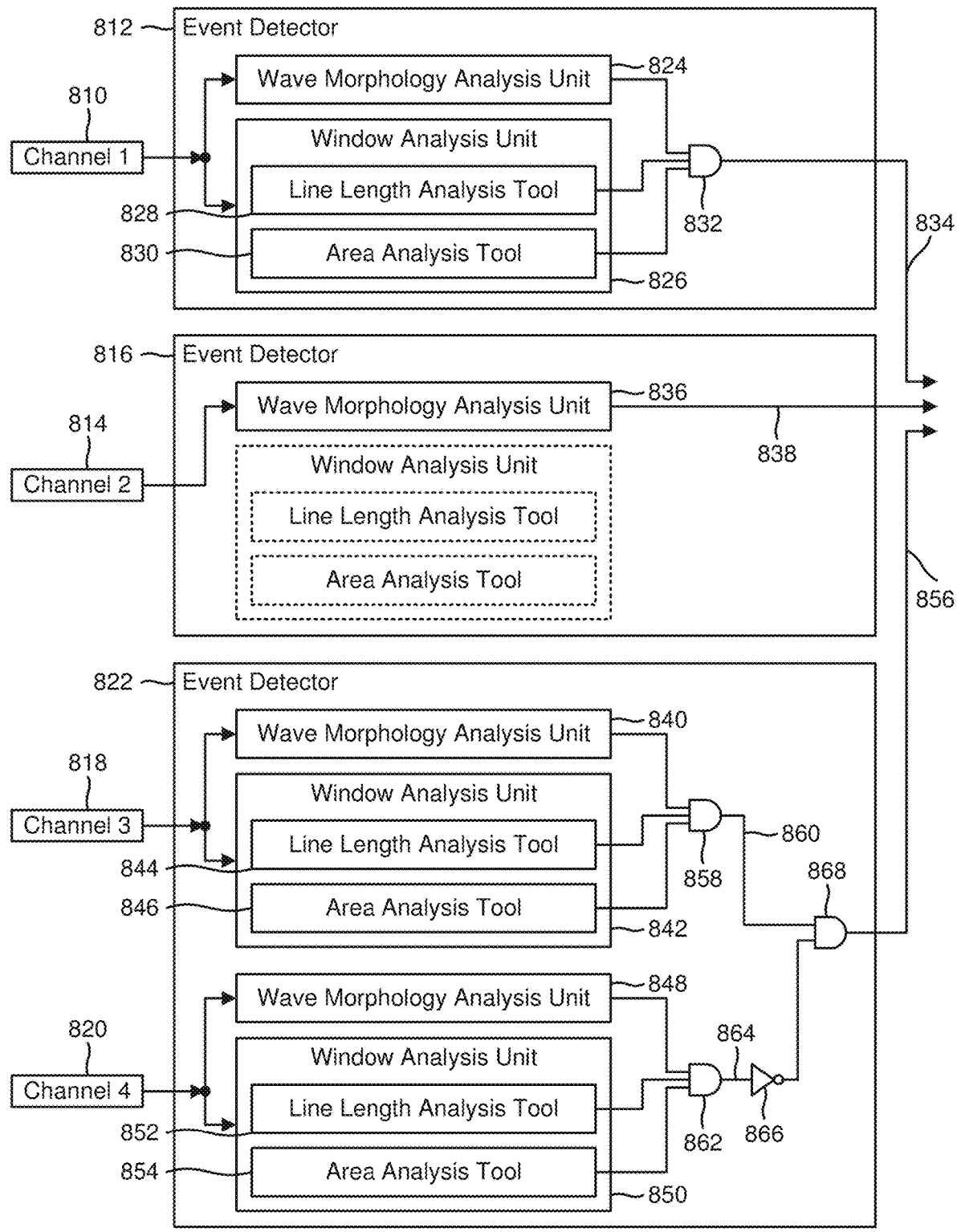
FIG. 8 is a block diagram illustrating the functional arrangement of components of the waveform analysis of the detection subsystem of FIG. 5 in one possible programmed embodiment of the invention.

The operation of the event detector logic 716 is illustrated in detail in the functional block diagram of FIG. 8, in which four exemplary sensing channels are analyzed by three illustrative event detectors. A first sensing channel 810 provides input to a first event detector 812. While the first event detector 812 is illustrated as a functional block in the block diagram of FIG. 8, it should be recognized that it is a functional block only for purposes of illustration, and may not have any physical counterpart in a device according to the invention. Similarly, a second sensing channel 814 provides input to a second event detector 816, and a third input channel 818 and a fourth input channel 820 both provide input to a third event detector 822.

Figure 7:
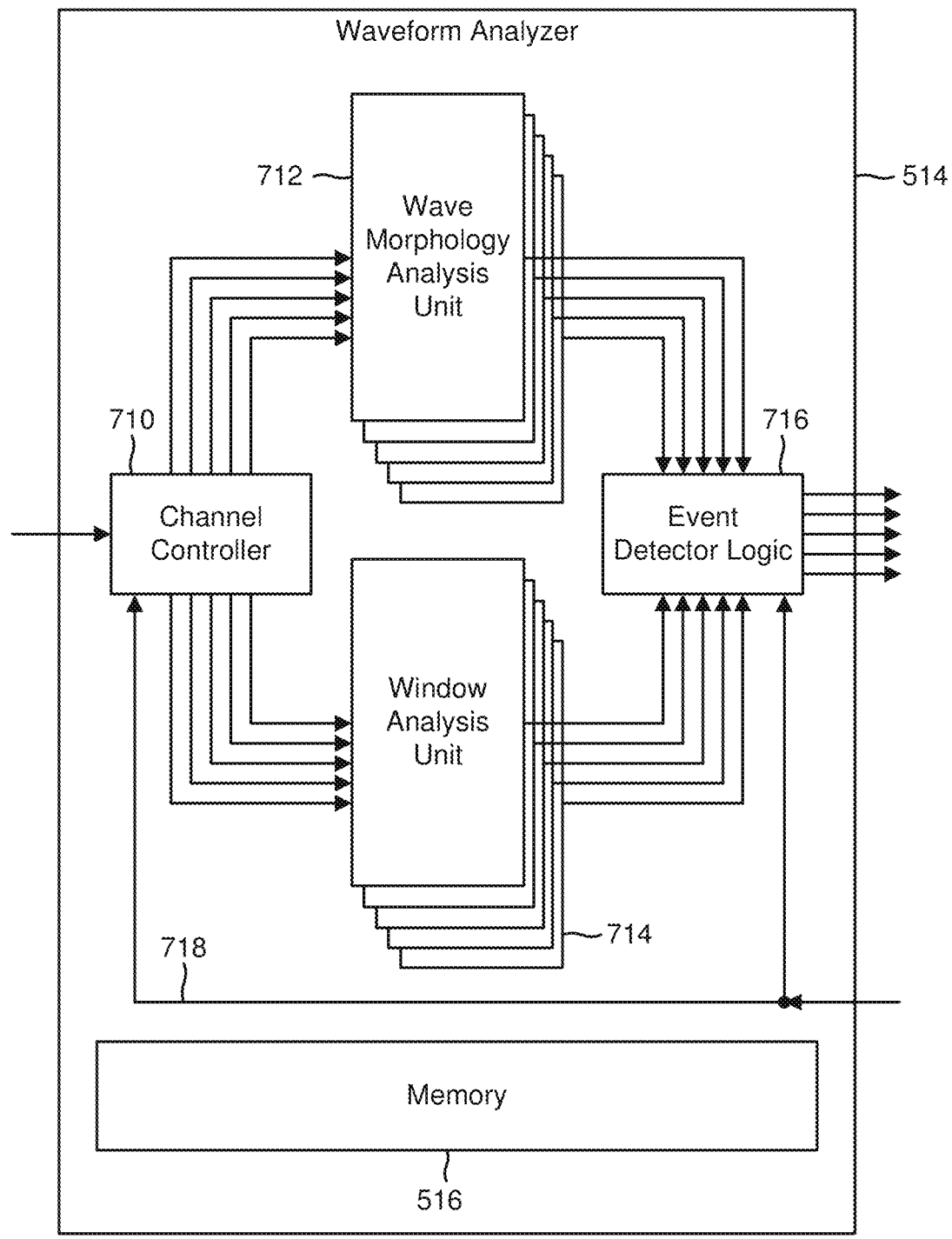
FIG. 7 is a block diagram illustrating the components of the waveform analyzer of the detection subsystem of FIG. 5.

Considering the processing performed by the event detectors 812, 816, and 822, the first input channel 810 feeds a signal to a wave morphology analysis unit 824 (one of the wave morphology analysis units 712 of FIG. 7) and a window analysis unit 826 (one of the window analysis units 714 of FIG. 7). The window analysis unit 826, in turn, includes a line length analysis tool 828 and an area analysis tool 830. The line length analysis tool 828 and the area analysis tool 830 analyze different aspects of the signal from the first input channel 810 as described in described in U.S. Pat. No. 6,810,285, previously incorporated by reference herein.

Outputs from the wave morphology analysis unit 824, the line length analysis tool 828, and the area analysis tool 830 are combined in a Boolean AND operation 832 and sent to an output 834 for further use by a system according to the invention. For example, if a combination of analysis tools in an event detector identifies several simultaneous (or near-simultaneous) types of activity in an input channel, a system according to the invention may be programmed to perform an action in response thereto.

In the second event detector 816, only a wave morphology analysis unit 836 is active. Accordingly, no Boolean operation needs to be performed, and the wave morphology analysis unit 836 directly feeds an event detector output 838. The third event detector 822 operates on two input channels 818 and 820, and includes two separate detection channels of analysis units: a first wave morphology analysis unit 840 and a first window analysis unit 842, the latter including a first line length analysis tool 844 and a first area analysis tool 846; and a second wave morphology analysis unit 848 and a second window analysis unit 850, the latter including a second line length analysis tool 852 and a second area analysis tool 854. The two detection channels of analysis units are combined to provide a single event detector output 856.

In the first detection channel of analysis units 840 and 842, outputs from the first wave morphology analysis unit 840, the first line length analysis tool 844, and the first area analysis tool 846 are combined via a Boolean AND operation 858 into a first detection channel output 860. Similarly, in the second detection channel of analysis units 848 and 850, outputs from the second wave morphology analysis unit 848, the second line length analysis tool 852, and the second area analysis tool 854 are combined via a Boolean AND operation 862 into a second detection channel output 864. In the illustrated embodiment of the invention, the second detection channel output 864 is invertible with selectable Boolean logic inversion 866 before it is combined with the first detection channel output 860. Subsequently, the first detection channel output 860 and the second detection channel output 864 are combined with a Boolean AND operation 868 to provide a signal to the output 856. In an alternative embodiment, a Boolean OR operation is used to combine the first detection channel output 860 and the second detection channel output 864.

In one embodiment of the invention, the second detection channel (analysis units 848 and 850) represents a "qualifying channel" with respect to the first detection channel (analysis units 840 and 842). In general, a qualifying channel allows a detection to be made only when both channels are in concurrence with regard to detection of an event. For example, a qualifying channel can be used to indicate when a seizure has "generalized," i.e. spread through a significant portion of a patient's brain. To do this, the third input channel 818 and the fourth input channel 820 are configured to receive EEG waveforms from separate amplifier channels coupled to electrodes in separate parts of the patient's brain (e.g., in opposite hemispheres). Accordingly, then, the Boolean AND operation 868 will indicate a detection only when the first detection output 860 and the second detection output 864 both indicate the presence of an event (or, when Boolean logic inversion 866 is present, when the first detection output 860 indicates the presence of an event while the second detection output 864 does not). As will be described in further detail below, the detection outputs 860 and 864 can be provided with selectable persistence (i.e., the ability to remain triggered for some time after the event is detected), allowing the Boolean AND combination 868 to be satisfied even when there is not precise temporal synchronization between detections on the two channels.

It should be appreciated that the concept of a "qualifying channel" allows the flexible configuration of a device 110 according to the invention to achieve a number of advantageous results. In addition to the detection of generalization, as described above, a qualifying channel can be configured, for example, to detect noise so a detection output is valid only when noise is not present, to assist in device configuration in determining which of two sets of detection parameters is preferable (by setting up the different parameters in the first detection channel and the second detection channel, then replacing the Boolean AND combination with a Boolean OR combination), or to require a specific temporal sequence of detections (which would be achieved in software by the CPU 428 after a Boolean OR combination of detections). There are numerous other possibilities.

The outputs 834, 838, and 856 of the event detectors are preferably represented by Boolean flags, and as described below, provide information for the operation of a system according to the invention.

While FIG. 8 illustrates four different sensing channels providing input to four separate detection channels, it should be noted that a maximally flexible embodiment of the present invention would allow each sensing channel to be connected to one or more detection channels. It may be advantageous to program the different detection channels with different settings (e.g., thresholds) to facilitate alternate "views" of the same sensing channel data stream.

Figure 9:
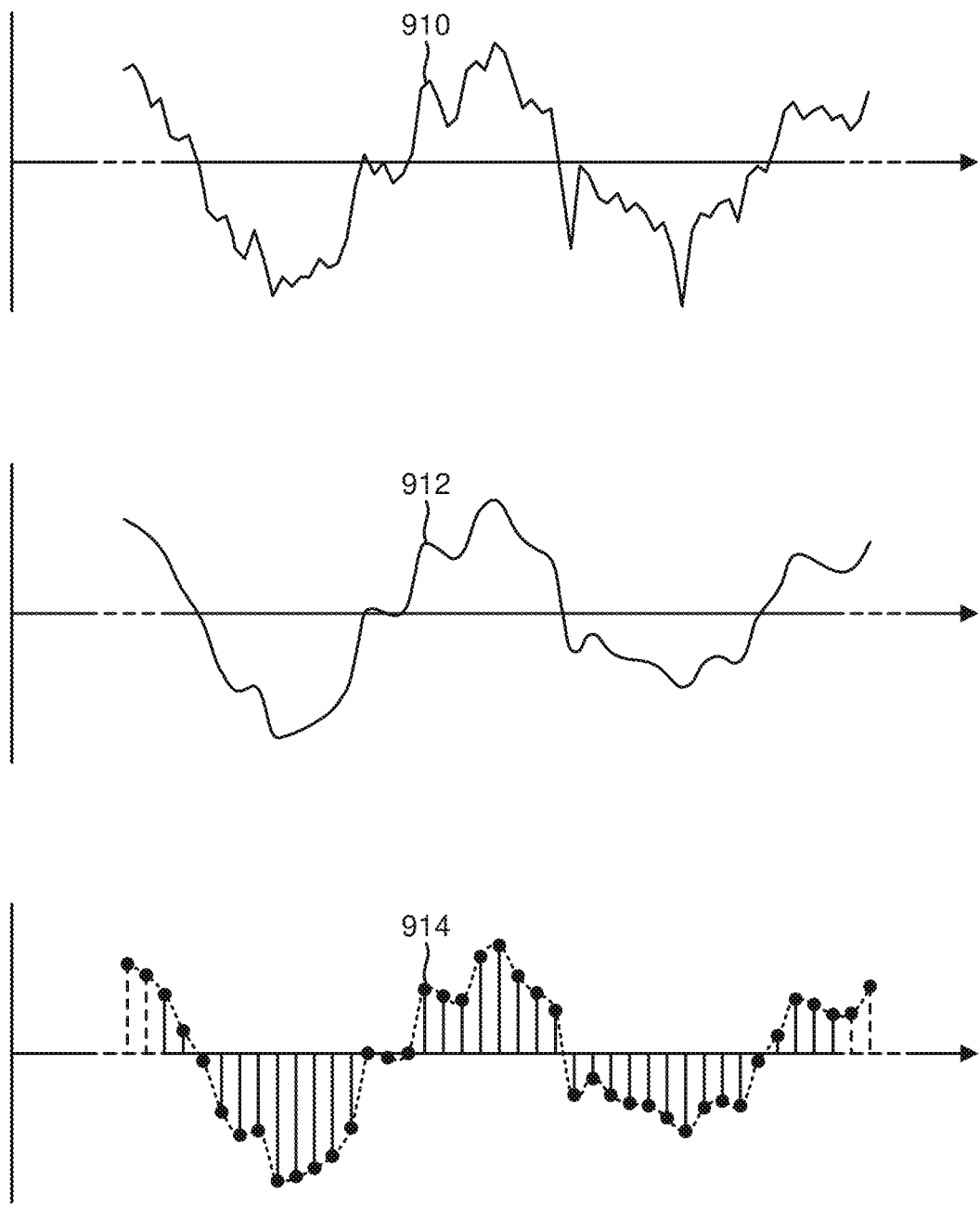
FIG. 9 is a graph of an exemplary EEG signal, illustrating decomposition of the signal into time windows and samples.

FIG. 9 illustrates three representative waveforms of the type expected to be manipulated by a system according to the invention. It should be noted, however, that the waveforms illustrated in FIG. 9 are illustrative only, and are not intended to represent any actual data. The first waveform 910 is representative of an unprocessed electroencephalogram (EEG) or electrocorticogram (ECoG) waveform having a substantial amount of variability; the illustrated segment has a duration of approximately 160 ms and a dominant frequency (visible as the large-scale crests and valleys) of approximately 12.5 Hz. It will be recognized that the first waveform is rather rough and peaky; there is a substantial amount of high-frequency energy represented therein.

The second waveform 912 represents a filtered version of the original EEG waveform 910. As shown, most of the high-frequency energy has been eliminated from the signal, and the waveform 912 is significantly smoother. In the disclosed embodiment of the invention, this filtering operation is performed in the sensing front end 512 before the analog to digital converters 612 (FIG. 6).

The filtered waveform 912 is then sampled by one of the analog to digital converters 612; this operation is represented graphically in the third waveform 914 of FIG. 9. As illustrated, a sample rate used in an embodiment of the invention is 250 Hz (4 ms sample duration), resulting in approximately 40 samples over the illustrated 160 ms segment. As is well known in the art of digital signal processing, the amplitude resolution of each sample is limited; in the disclosed embodiment, each sample is measured with a resolution of 10 bits (or 1024 possible values). As is apparent upon visual analysis of the third waveform, the dominant frequency component has a wavelength of approximately 20 samples, which corresponds to the dominant frequency of 12.5 Hz.

Referring now to FIGS. 10A-10D, the processing of a type of wave morphology analysis unit 712, referred to as a half wave detector, is described in conjunction with a filtered and sampled waveform 1000 of the type illustrated as the third waveform 914 of FIG. 9. A half wave detector looks for and counts "half waves" when they occur in a predetermined window of time in an electrographic signal (e.g., a signal corresponding to a time-varying field potential difference between two electrodes, at least one of which is implanted in or on a patient's brain). What constitutes a half wave that should be counted is defined so that the counts that result from running the algorithm roughly correlate to the power of the signal at a particular dominant frequency (or in a particular frequency band). A half wave detector is useful, for example, in applications of an implantable medical device system to detect electrographic activity corresponding to epileptiform activity or the onset of a seizure. It should be appreciated that a half wave detector may be used in analyzing waveforms corresponding to physiological data sensed from a patient for different types of activity or different features in the sensed data. For example, when the patient has epilepsy, some instances of a waveform analyzer implemented as a half wave detector may be configured to detect rhythmic activity when it occurs in electrographic signals monitored from the patient and other instances of a waveform analyzer implanted as a half wave detector may be configured to detect spike complexes when these occur in the electrographic signals. Thus, the parameters and the values for the parameters may vary for different iterations of the same detection tool, depending upon the nature and type of activity each iteration of the tool is intended to detect.

A half wave detector may have several programmable parameters to define half wave detection: namely, a half wave hysteresis parameter, one or more half wave amplitude parameters, one or more half wave duration parameter (also referred to sometimes as a "half wave width parameter"), a half wave count criterion parameter, a half wave window size parameter, a qualified analysis window count parameter, and a detection analysis window size parameter. These parameters may be thought of as being part of the "parameter space" for a tool to detect half waves in a signal.

"Half waves" generally, as well as half wave hysteresis, will now be described with reference to FIGS. 10A and 10B. A waveform 1000 corresponds to an electrographic signal after the electrographic signal has been pre-processed and quantized (i.e., subjected to pre-processing and conditioning such as filtering to remove low and high frequency energy and sampling by an analog-to-digital converter). The y-axis corresponds to units of amplitude (which may ultimately be correlated to voltage or current), and the x-axis corresponds to units of time, more particular, fractions of a second.

Figure 10A:
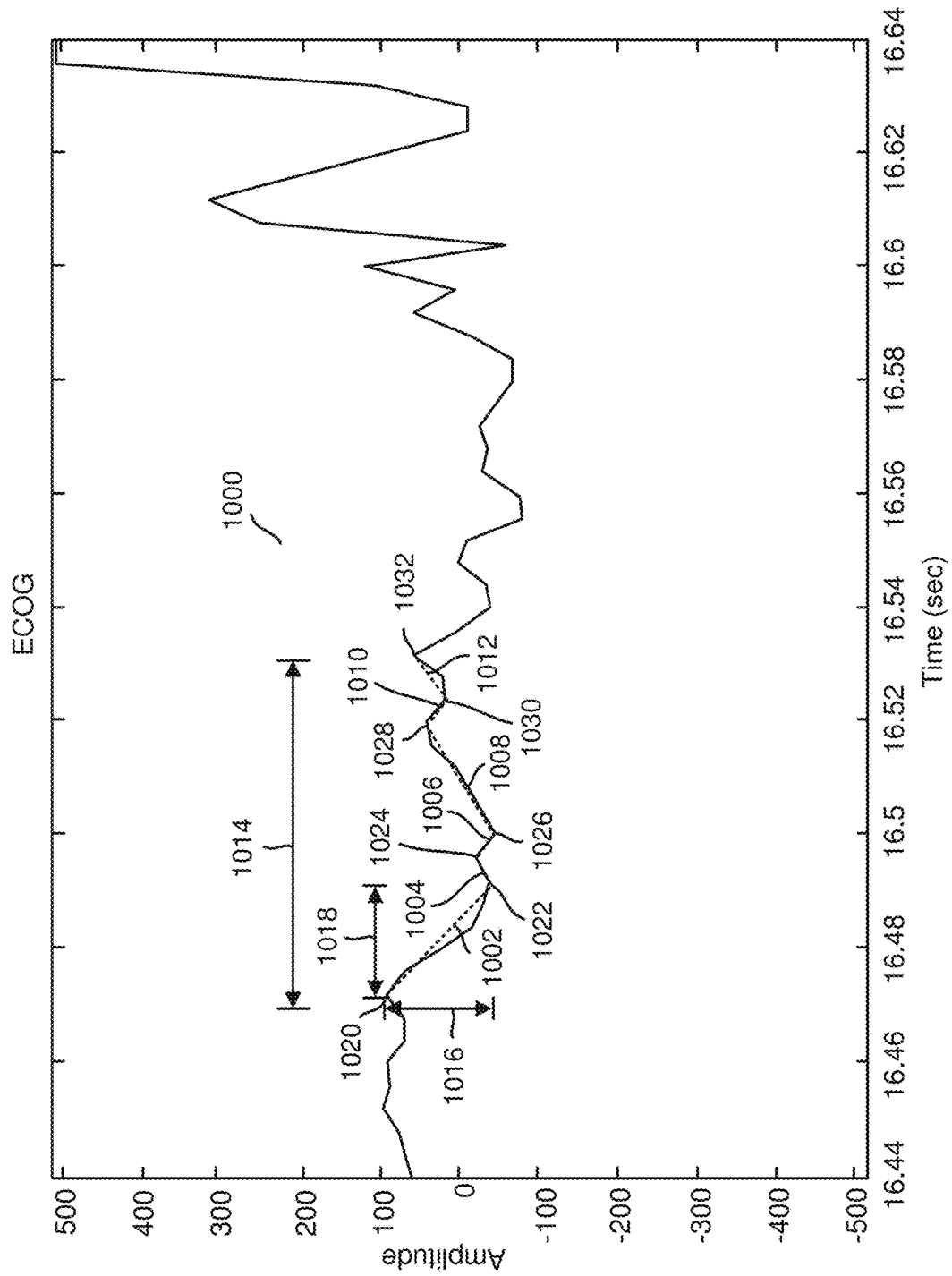
FIG. 10A is a graph of a time-series representation of an EEG signal exhibiting a plurality of transitions in the direction of the signal.

If a half wave of the waveform is defined generally as the excursion of the signal over time from a local minimum to a next local maximum or, alternatively, from a local maximum to a next local minimum, it will be appreciated that in FIG. 10A there are six half waves 1002, 1004, 1006, 1008, 1010, and 1012 (associated with the dashed lines) in the waveform segment 1014 that extends over about a 60 ms interval between about 16.47 and 16.53 s.

A given half wave may be characterized by an amplitude and a duration (also referred to sometimes as a "width"), such that a half wave amplitude is the difference between the local maximum and minimum amplitudes, and the half wave duration is the period of time from the beginning of a half wave to the end of the half wave. A half wave further may be characterized by a direction based on whether the slope of the half wave is positive or negative (determined from the positions of the starting point and ending point of a given half wave on the horizontal axis as compared to the vertical axis). In FIG. 10A, for example, the half wave 1002 has an amplitude 1016 of about 130 units (from about +100 units to about −30 units), a duration 1018 of about 20 ms (from about 16.47 s to about 16.49 s), and a negative slope. Accordingly, in FIG. 10A, a half wave #1 1002 may be represented by a vector corresponding to the dashed line from the local maximum at the starting point 1020 to the next local minimum at the ending point 1022. At the point 1022, the waveform changes direction, with a positive slope towards point 1024 that marks the end of the half wave #2 1004 and the beginning of the half wave #3 1006. The points 1026, 1028, 1030, and 1032 define the end of the half wave #3 1006 and the beginning and end of the half wave #4 1008, the half wave #5 1010, and the half wave #6 1012, respectively.

It may be desirable to configure a given half wave algorithm to ignore some half waves that are deemed to be insignificant variations (or small perturbations) in the waveform so that these will not, in fact, be recognized by the detection tool as half waves. In a half wave detector, this may be accomplished by defining a value for a hysteresis parameter in the half wave detection algorithm. In FIG. 10A, features of the waveform that are deemed to constitute insignificant variations in the electrographic signal might correspond to the half wave #2 1004, the half wave #3 1006, the half wave #5 1010, and the half wave #6 1012. These half waves might be, for example, deemed to be inconsistent with the overall movement of the electrographic signal, and/or attributed to perturbations in the signal that result from quantizing of noise or other low-amplitude signal components of the sensed physiological signal.

Thus, a hysteresis setting may correspond to allowing some half waves in the direction of movement of the waveform to be disregarded and thus not treated as a reversal of direction that warrants identifying the reversal of direction point as the starting (or ending) point of a half wave. A hysteresis allowance in a detection algorithm can be used, for example, to avoid having to subject the physiological signals being sensed from the patient to more rigorous processing and conditioning before the signals are introduced to the algorithm.

The effect of specifying a value for a hysteresis parameter may be appreciated with reference to FIG. 10B. FIG. 10B represents the same waveform 1000 of FIG. 10A, but now there are only two dashed lines representing vectors corresponding to two half waves in the waveform segment 1014. More particularly, one half wave 1040 (hereinafter referred to as second half wave 1040 in FIG. 10C) extends from a starting point 1020 to an ending point 1026, and another half wave 1042 (hereinafter referred to as third half wave 1042 in FIG. 10C) extends from the point 1026 to another half wave ending point 1032. In this example, the half wave hysteresis parameter has been set to specify a minimum amplitude that the waveform has to exceed when it transitions from one direction to the other (e.g., positive to negative slope) before the half wave will be considered to represent the start or end of a half wave.

More specifically, in the example of FIG. 10B, the half wave hysteresis parameter has been set to a value of 50 amplitude units such that, if after the signal comprising the waveform changes slope, the amplitude of the half wave never exceeds 50 amplitude units before it changes slope again, no half wave will be deemed to have ended or begun. Since the half wave #2 1004, the half wave #3 1006, the half wave #5 1010 and the half wave #6 1012 shown in FIG. 10A each are characterized by an amplitude of less than 50 units, when the half wave hysteresis parameter has been set to a value of 50 amplitude units, each of these half waves will be ignored in determining which and how many half waves are present in the waveform segment 1014. Thus, the half wave 1040 (the second half wave 1040 in FIG. 10C) has an amplitude of about 150 units (from about +100 units to about −50 units on the vertical y-axis) and a half wave duration of about 30 ms (from about 16.47 s to about 16.50 s), and a negative slope. The half wave 1042 (the third half wave 1042 in FIG. 10C) has an amplitude of about 100 units (from about −50 units to about +50 units) and a half wave duration of about 30 ms (from about 16.50 to about 16.53 s) and a positive slope.

In addition to using parameters and values for the same to decide when a half wave will be deemed to begin and end, parameters are used to determine which half waves occurring in a given processing window are to be considered "qualified half waves," such that they will be treated in a particular way by the algorithm. A processing window may be defined as being that which is appropriate for the circumstance, given the specifications of the relevant hardware and software. By way of example, a processing window specified for a half wave detector may correspond to a 128 ms window, which may in turn represent 32 samples of the physiological data (e.g., of an electrographic signal sensed from the patient) at a 250 Hz sampling rate.

In one implementation, referred to as a "two-parameter implementation," a half wave is considered a "qualified half wave" based on a set of minimum-value parameters corresponding to a minimum half wave amplitude parameter and a minimum half wave duration parameter. In this case, if the amplitude of the half wave exceeds the minimum half wave amplitude parameter, and the duration of the half wave exceeds the minimum half wave duration parameter, the half wave is considered a "qualified half wave."

In another implementation, referred to as a "four-parameter implementation," a half wave may be considered a "qualified half wave" based on a set of minimum-value parameters corresponding to a minimum half wave amplitude parameter and a minimum half wave duration parameter, and a set of maximum-value parameters corresponding to a maximum half wave amplitude parameter and a maximum half wave duration parameter. In this case, if the amplitude of the half wave exceeds the minimum half wave amplitude parameter but does not exceed the maximum half wave amplitude, and the duration of the half wave exceeds the minimum half wave duration parameter but does not exceed the maximum half wave duration parameter, the half wave is considered a "qualified half wave."

In yet another implementation, referred to as an "eight-parameter implementation," a half wave may be considered a "qualified half wave" based on different criteria for positive-slope half waves and negative-slope half waves. For example, a half wave having a positive slope may be considered a "qualified half wave" if its amplitude exceeds a positive-slope minimum half wave amplitude parameter but does not exceed a positive-slope maximum half wave amplitude, and its duration exceeds a positive-slope minimum half wave duration parameter but does not exceed a positive-slope maximum half wave duration. Likewise, a half wave having a negative slope may be considered a "qualified half wave" if its amplitude exceeds a negative-slope minimum half wave amplitude parameter but does not exceed a negative-slope maximum half wave amplitude parameter, and its duration exceeds a negative-slope minimum half wave duration parameter but does not exceed a negative-slope maximum half wave duration parameter.

Two-Parameter Implementation:

As noted above, in the two parameter implementation, a half wave is considered a "qualified half wave" based on a set of minimum-value parameters corresponding to a minimum half wave amplitude parameter and a minimum half wave duration parameter. In this case, if the amplitude of the half wave exceeds the minimum half wave amplitude parameter, and the duration of the half wave exceeds the minimum half wave duration parameter, the half wave is considered a "qualified half wave."

The range of values for the minimum half wave amplitude parameter will normally be consistent with the range of possible amplitudes for the waveform corresponding to the sensed physiological data. In the example of FIG. 10C, and with reference to the y-axis of FIG. 10C, the range of possible amplitudes is +/−512 units of amplitude.

The minimum half wave duration parameter is the parameter that determines what maximum frequency represented in the waveform will be detected by the half wave detector. The range of values for the minimum half wave duration will normally be between 0 ms (corresponding to 125 Hz for a sampling rate of 250 Hz) and 400 ms (corresponding to approximately 1 Hz for a sampling rate of 250 Hz). The value for the minimum half wave duration parameter will be driven, at least in part, by the rate at which the data is sampled by the system. In an example, if a signal is being sampled at 250 Hz, then each sample will be 4 ms apart. If the value of the minimum half wave duration is set at 4 ms, then each half wave would have to last longer than 4 ms in order to be considered a qualified half wave. Since each sample is 4 ms, then a qualified half wave would have to endure for two samples, which would correspond to an effective minimum half wave duration of 8 ms. If a whole wave is defined as comprising two consecutive qualified half waves characterized by opposite slopes, then a whole wave would have to be represented by four samples of 4 ms each, or 16 ms total.

For an electrographic signal sensed from a patient and quantized by a neurostimulator, the frequency of the signal may be approximated as the inverse of the duration of a whole wave. In an example, if a whole wave takes four 4 ms samples to be represented, and since $1/16$ ms is 62.5 Hz, a half wave detector with the value of the minimum half wave duration parameter set at 4 ms will not be configured to detect the activity in an electrographic signal that is characterized by a frequency of greater than 62.5 Hz.

Referring now to FIG. 10C, the waveform 1000 is shown extending from about 16.44 s to about 16.64 s (or for about 200 ms). The half wave hysteresis parameter is set at 50 units, such that a transition in the waveform that corresponds to a increase or decrease in amplitude of less than 50 units will not be identified as a discrete half wave but rather will be included as part of a greater amplitude half wave. There are eleven half waves in the waveform 1000, namely, a first half wave 1050, the second half wave 1040 (first shown in FIG. 10B), the third half wave 1042 (first shown in FIG. 10B), a fourth half wave 1052, a fifth half wave 1054, a sixth half wave 1056, a seventh half wave 1058, an eighth half wave 1060, a ninth half wave 1062, a tenth half wave 1064, and an eleventh half wave 1066.

A detector can be implemented to target a very specific pattern like the one formed by the eighth half wave 1060 and the ninth half wave 1062. If the minimum half wave amplitude parameter is set at a value of 150 units and the minimum half wave duration parameter is set at a value of 0 ms, then with reference to Table 1 below, only seven of the eleven half waves (HW) in the waveform segment 1068 will constitute "qualified half waves," namely, the second half wave 1040, the fourth half wave 1052, the fifth half wave 1054, the eighth half wave 1060, the ninth half wave 1062, the tenth half wave 1064, and the eleventh half wave 1066. That is, only seven of the eleven half waves meet or exceed the thresholds of both the minimum half wave amplitude parameter and the minimum half wave duration.

TABLE 1

| | $1^{st}$ HW 1050 | $2^{nd}$ HW 1040 | $3^{rd}$ HW 1042 | $4^{th}$ HW 1052 | $5^{th}$ HW 1054 | $6^{th}$ HW 1056 | $7^{th}$ HW 1058 | $8^{th}$ HW 1060 | $9^{th}$ HW 1062 | $10^{th}$ HW 1064 | $11^{th}$ HW 1066 |
|---|---|---|---|---|---|---|---|---|---|---|---|
| Min. HW Amp. (150 units)? | No | Yes | No | Yes | Yes | No | No | Yes | Yes | Yes | Yes |
| Min. HW Duration (0 ms)? | Yes | Yes | Yes | Yes | Yes | Yes | Yes | Yes | Yes | Yes | Yes |
| Qualified HW? | No | Yes | No | Yes | Yes | No | No | Yes | Yes | Yes | Yes |

For example, while the first half wave 1050 exceeds the 0 ms threshold value for the minimum half wave duration parameter, it does not also exceed the 150 units threshold value for the minimum half wave amplitude parameter, so the first half wave 1050 is not identified as a qualified half wave. Similarly, the sixth half wave 1056 exceeds the 0 ms threshold value for the minimum half wave duration parameter, but it does not exceed the 150 unit threshold value for the minimum half wave amplitude parameter, so the sixth half wave is not identified as a qualified half wave. Each of the second half wave 1040, the fourth half wave 1052, the fifth half wave 1054, the eighth half wave 1060, the ninth half wave 1062, the tenth half wave 1064, and the eleventh half wave 1066 satisfy both the minimum half wave amplitude parameter and minimum half wave duration thresholds, so each of these seven half waves is identified as a qualified half wave.

Two other parameters that may be specified for a half wave detector relate to the how much of a given frequency has to occur, at a minimum, in a particular time period in order for the algorithm to determine whether to register something as having been 'detected' (e.g., the onset of epileptiform activity in the patient). These two parameters will be described with reference to FIG. 10D and include a half wave count criterion parameter and a half wave window size parameter. The half wave count criterion parameter and the half wave window size parameter allow a half wave detector to identify a "qualified analysis window". Generally, the number of qualified half waves has to exceed the value selected for the half wave count criterion parameter during the time window defined by the value selected for the half wave window size parameter, in order for the algorithm to consider the circumstance a detection-worthy circumstance. When, in a given half wave window with a duration specified by the half wave window size parameter, the number of qualified half waves exceeds the value for the half wave count criterion parameter, then that analysis window which contains the end of the half wave window is considered a "qualified analysis window".

In one example, a value of 9 might be set for the half wave count criterion parameter and a value of 1 s (1000 ms) may be set for the half wave window size parameter. In the algorithm, these values would mean that at least 10 qualified half waves have to occur in 1 s (or at least five whole waves in 1 s) in order for the minimum frequency criteria for detection to be considered to have been met (five whole waves in one second corresponds to a frequency of 5 Hz).

Figure 10D:
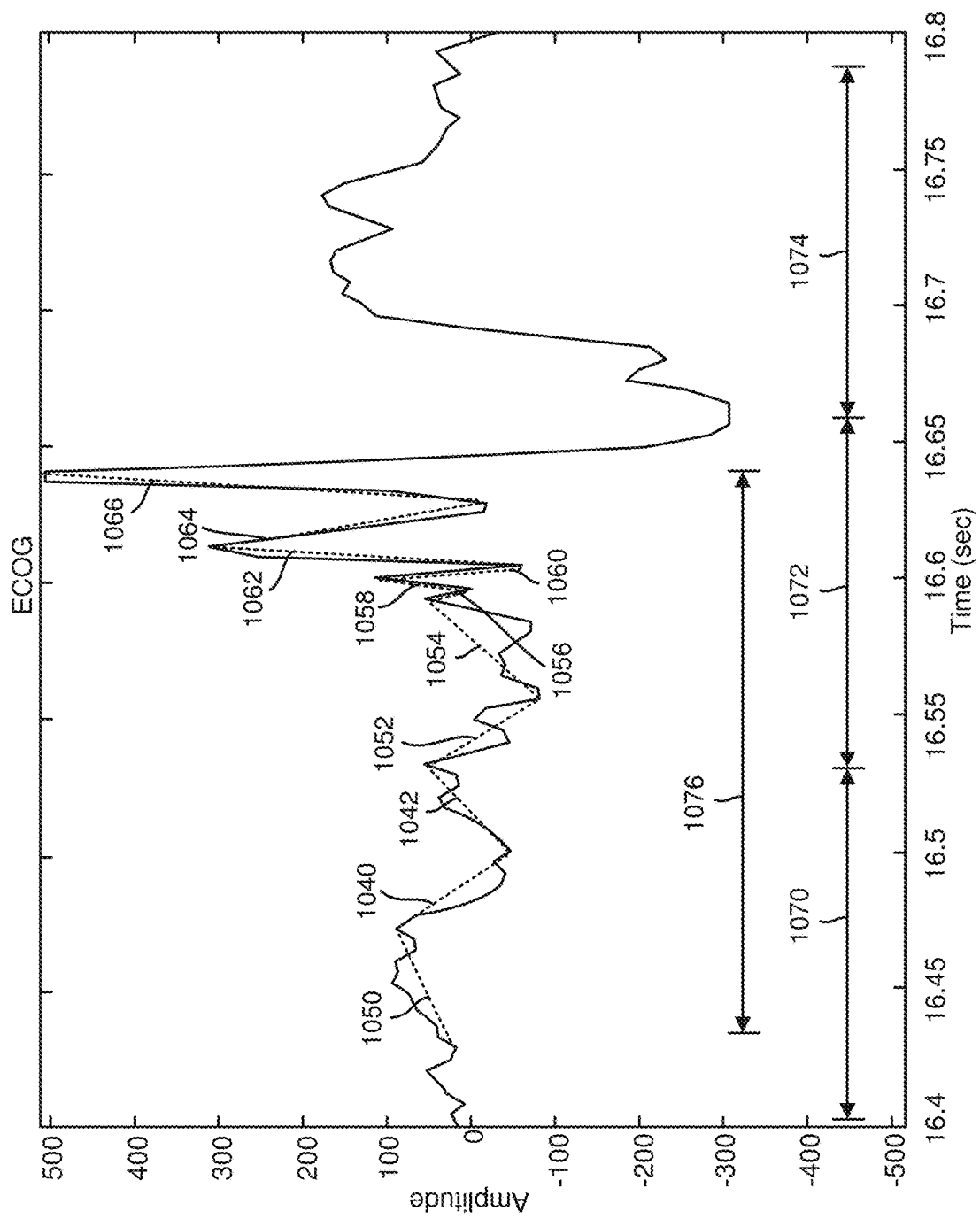
FIG. 10D is the graph of FIG. 10C in which parameters of a method for identifying a minimum frequency are illustrated.

In another example, a value of 6 might be set for the half wave count criterion and a value of 200 ms might be set for the half wave window size. Referring now to FIG. 10D, at the base of the graph along the x-axis (time in seconds), three sets of double-headed arrows indicate three consecutive processing or analysis windows of 128 ms each, namely, analysis window #1 1070, analysis window #2 1072, and analysis window #3 1074. Analysis window #1 1070 begins at about 16.40 s and ends at about 16.53 s, analysis window #2 1072 runs from about 16.53 s to about 16.66 s, and analysis window #3 1074 runs from about 16.66 s to about 16.79 s.

Based on a half wave hysteresis parameter set at 50 units of amplitude, minimum half wave amplitude parameter set at 150 units, and a minimum half wave duration parameter set at 0 ms, the algorithm identifies and counts qualified half waves within a 200 ms half wave window 1076 that ends at about 16.64 s. Since there are seven qualified half waves in the 200 ms half wave window 1076 (see also FIG. 10C and Table 1 and the descriptions thereof), then the minimum frequency for detection has been met (more than six qualified half waves counted in a half wave window of 200 s). When the seventh qualified half wave occurred, the system was in the second 128 ms analysis window shown in FIG. 10D, or analysis window #2 1072. Thus, analysis window #2 1072 is a "qualified analysis window".

Four-Parameter Implementation:

As noted above, in a four-parameter implementation of qualified half wave detection, a half wave may be considered a "qualified half wave" based on a set of minimum-value parameters corresponding to a minimum half wave amplitude parameter and a minimum half wave duration parameter, and a set of maximum-value parameters corresponding to a maximum half wave amplitude parameter and a maximum half wave duration parameter. In this case, if the amplitude of the half wave exceeds the minimum half wave amplitude parameter but does not exceed the maximum half wave amplitude, and the duration of the half wave exceeds the minimum half wave duration parameter but does not exceed the maximum half wave duration parameter, the half wave is considered a "qualified half wave." In this way, besides doing a filtering in the frequency domain (valid for sine-wave signals), there is an amplitude filtering in the time domain, where the band-passed amplitudes are those within the interval [minimum half wave amplitude, maximum half wave amplitude].

Figure 17:
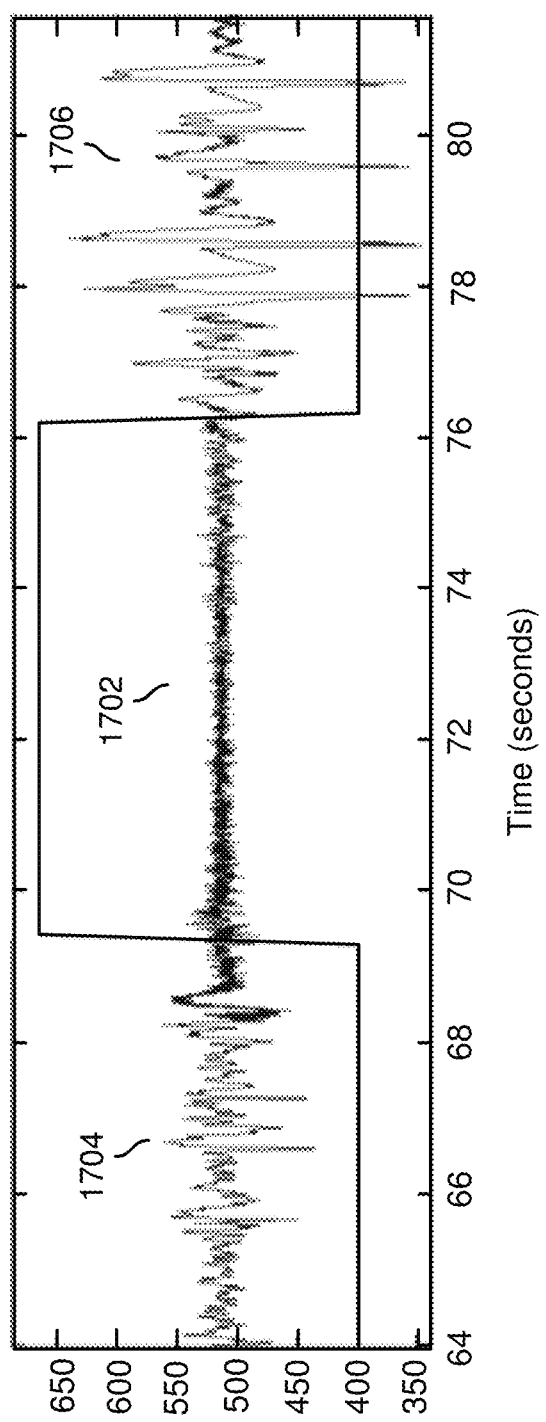
FIG. 17 is a graphical illustration of an EEG including low amplitude fast frequency activity and high amplitude fast frequency activity.

In this implementation, a half wave is qualified if its duration (width) and amplitude fall within the intervals:
[minHWDur, maxHWDur], and
[minHWAmp, maxHWAmp],
where: minHWDur=minimum half wave duration
maxHWDur=maximum half wave duration
minHWAmp=minimum half wave amplitude
maxHWAmp=maximum half wave amplitude Including the maximum half wave amplitude and maximum half wave duration parameters in the half wave detection tool allows the half wave detection tool to detect specific low fast frequency activity patterns (typically present before seizures), including for example, single spikes, a train of spikes, and any other pattern, repetitive or not, while substantially avoiding detection of other activity. For example, with reference to FIG. 17, a low fast frequency activity pattern 1702 may be bounded on either side by high amplitude fast frequency activity 1704, 1706. The half waves within the low fast frequency activity pattern 1702 may be characterized uniquely by a peak-to-peak amplitude and a duration that allows for detection and qualification of such half waves while avoiding detection and qualification of high amplitude fast frequency activity half waves. Peak-to-peak amplitude refers to the magnitude of the difference between the minimum amplitude of a low fast frequency activity half wave and the maximum amplitude of the low fast frequency activity half wave. For example, with reference to FIG. 10A, low fast frequency activity half wave 1002 has a peak-to-peak amplitude 1016. Duration refers to the duration of a low fast frequency activity pattern. For example, with reference to FIG. 10A, low fast frequency activity half wave 1002 has a duration 1018.

An issue that may arise when there is no maximum half wave parameter (e.g., such as in the case of the above described two parameter implementation) is that high amplitude fast frequency activity may also be detected, which will not be differentiated from low fast frequency activity. For example, with reference to FIG. 17, detection and qualification by a low fast frequency event detection tool, of half waves in high amplitude fast frequency activity 1704, 1706 may lead to inaccurate counting of qualified low fast frequency half waves, which may in turn lead to detection of false positive neurological events by the low fast frequency event detector. Including a maximum half wave parameter provides for a more refined detection tool that: 1) reduces the likelihood of detecting activity other than low fast frequency activity; and 2) provides for a more accurate classification of qualified low fast frequency half waves. These properties 1) and 2) may increase the specificity (lower false positive detections) and sensitivity (lower false negative detections) and possibly improve detection timing (earlier detections), for the particular pattern, e.g., low fast frequency, detection being detected by the detection tool. Such an improvement in event detection provides improved responsive stimulation and thus overall improved patient therapy.

In the example of FIG. 10C, and with reference to the y-axis of FIG. 10C, the range of possible amplitudes is +/−512 units of amplitude. Within this range, the range of values for the minimum half wave amplitude parameter may be between 0 units and 1022 units, and the range of values for the maximum half wave amplitude parameter may be between 0 units and 1023 units with the restriction that the minimum half wave amplitude parameter is always lower than the maximum half wave amplitude parameter.

The minimum half wave duration parameter is the parameter that determines what maximum frequency represented in the waveform will be detected by the half wave detector. The range of values for the minimum half wave duration parameter may be between 0 ms (corresponding to 125 Hz for a sampling rate of 250 Hz) and 386 ms (corresponding to approximately 1 Hz for a sampling rate of 250 Hz).

The maximum half wave duration parameter is the parameter that determines more specifically what the minimum frequency represented in the waveform will be detected by the half wave detector. The range of values for the maximum at a value of 0 ms, and the maximum half wave duration parameter is set at a value of 16 ms, then with reference to Table 2 below, only three of the eleven half waves in the waveform segment 1068 will constitute "qualified half waves," namely, the eighth half wave 1060, the ninth half wave 1062, and the tenth half wave 1064. That is, only three of the eleven half waves fall within the amplitude interval defined by the minimum half wave amplitude parameter and the maximum half wave amplitude parameter, and the duration interval defined by the minimum half wave duration parameter and the maximum half wave duration parameter is set at a value of 16 ms.

TABLE 2

|  | $1^{st}$ HW 1050 | $2^{nd}$ HW 1040 | $3^{rd}$ HW 1042 | $4^{th}$ HW 1052 | $5^{th}$ HW 1054 | $6^{th}$ HW 1056 | $7^{th}$ HW 1058 | $8^{th}$ HW 1060 | $9^{th}$ HW 1062 | $10^{th}$ HW 1064 | $11^{th}$ HW 1066 |
|---|---|---|---|---|---|---|---|---|---|---|---|
| HW Amp. between Min. HW Amp. (150 units) and Max. HW Amp. (400 units) | No | Yes | No | Yes | Yes | No | No | Yes | Yes | Yes | No |
| HW Duration between Min. HW Duration (0 ms) and Max. HW Duration (16 ms)? | No | No | No | No | No | Yes | Yes | Yes | Yes | Yes | Yes |
| Qualified HW? | No | No | No | No | No | No | No | Yes | Yes | Yes | No | half wave duration parameter may be between 4 ms (corresponding to 62.5 Hz for a sampling rate of 250 Hz) and 400 ms (corresponding to approximately 1 Hz for a sampling rate of 250 Hz), with the restriction that the minimum half wave width parameter is always lower than the maximum half wave width parameter.

The value for the minimum half wave duration parameter and the maximum half wave duration parameter will be driven, at least in part, by the rate at which the data is sampled by the system. In an example, if a signal is being sampled at 250 Hz, then each sample will be 4 ms apart. If the value of the minimum half wave duration is set at 4 ms, then each half wave would have to last longer than 4 ms in order to be considered a qualified half wave. Since each sample is 4 ms, then a qualified half wave would have to endure for two samples, which would correspond to an effective minimum half wave duration of 8 ms. If a whole wave is defined as comprising two consecutive qualified half waves characterized by opposite slopes, then a whole wave would have to be represented by four samples of 4 ms each, or 16 ms total.

Referring again to FIG. 10C, the waveform 1000 is shown extending from about 16.44 s to about 16.64 s (or for about 200 ms), there are eleven half waves in the waveform 1000, namely, a first half wave 1050, the second half wave 1040 (first shown in FIG. 10B), the third half wave 1042 (first shown in FIG. 10B), a fourth half wave 1052, a fifth half wave 1054, a sixth half wave 1056, a seventh half wave 1058, an eighth half wave 1060, a ninth half wave 1062, a tenth half wave 1064, and an eleventh half wave 1066.

A detector can be implemented to target a very specific pattern like the one formed by the eighth half wave 1060 and the ninth half wave 1062. If the minimum half wave amplitude parameter is set at a value of 150 units, the maximum half wave amplitude parameter is set at a value of 400 units, the minimum half wave duration parameter is set As mentioned above, including the additional two parameters of maximum half wave amplitude and maximum half wave duration parameters in the half wave detection tool allows the half wave detection tool to detect qualified half waves corresponding to specific low fast frequency activity patterns, while avoiding detection of high amplitude fast frequency activity. This may improve the accuracy of detections of a particular pattern, e.g., low fast frequency. The foregoing may be applicable to other types of activity patterns, such as, for example gamma activity and spike activity. The parameters of the half wave detection tool may be tuned to different values depending on the activity desired to be detected. Examples of neurological event detections based on other types of activity patterns are provided below with reference to FIGS. 14A, 14B, 15, and 16.

Because the detections of qualified have waves are input to a neurological event detection tool, the improved accuracy of qualified half wave detections provided by the four-parameter half wave detection tool may improve the specificity and sensitivity of neurological event detections by the neurological event detection tool. A more specific and sensitive neurological event detection tool provides an improved implantable medical device that reduces both false positive detections of neurological events and false negatives. This is beneficial in responsive stimulation therapy in that stimulation is more likely to only be delivered upon a true detection of a true neurological event. The additional parameters do not much impact the computational complexity or power consumption of the neurological event detection tool because the extra computational steps resulting from the additional parameters are minimal and do not consume much more than existing neurological event detection tools.

Eight-Parameter Implementation:

As noted above, in a eight-parameter implementation of qualified half wave detection, a half wave may be considered a "qualified half wave" based on different criteria for positive-slope half waves and negative-slope half waves. For example, a half wave having a positive slope may be considered a "qualified half wave" if its amplitude exceeds a positive-slope minimum half wave amplitude parameter but does not exceed a positive-slope maximum half wave amplitude, and its duration exceeds a positive-slope minimum half wave duration parameter but does not exceed a positive-slope maximum half wave duration. Likewise, a half wave having a negative slope may be considered a "qualified half wave" if its amplitude exceeds a negative-slope minimum half wave amplitude parameter but does not exceed a negative-slope maximum half wave amplitude parameter, and its duration exceeds a negative-slope minimum half wave duration parameter but does not exceed a negative-slope maximum half wave duration parameter.

When considering sine-wave signals only, adding the maximum half wave amplitude and maximum half wave duration parameters indicated above in the four parameter implementation may be sufficient to accomplish a precise pattern recognition. However, intracranial EEG signals are not sine-wave signals. Accordingly, in the eight parameter implementation, different minimum and maximum half wave amplitude parameters and minimum and maximum half wave duration parameters are set for each of positive-slope half waves and for negative-slope half waves.

In this implementation, detected half waves have different qualification requirements depending on whether they have a positive slope or a negative slope. A negative slope half wave is qualified if its duration and amplitude fall within the intervals:
[minHWDur1, maxHWDur1], and
[minHWAmp1, maxHWAmp1], A positive slope half wave is qualified if its duration and amplitude fall within the intervals:
[minHWDur2, maxHWDur2], and
[minHWAmp2, maxHWAmp2].

Similar to the four-parameter implementation, including the maximum half wave amplitude and maximum half wave duration parameters in the half wave detection tool allows the half wave detection tool to detect specific low fast frequency activity patterns (typically present before seizures), including for example, single spikes, a train of spikes, and any other pattern, repetitive or not. Including a set of parameters for each of positive slope half waves and negative slope half waves may allow for even more specific detection of low fast frequency activity patterns.

An issue that may arise when the same set of minimum half wave amplitude parameter and maximum half wave amplitude parameter, and the same set of minimum half wave duration parameter and maximum half wave duration parameter are used for both positive and negative slope half waves is that high amplitude fast frequency activity may also be detected, which will not be differentiated from low fast frequency activity. Including different sets of parameters for positive slope half waves and negative slope half waves provides for an even more refined detection tool that: 1) reduces the likelihood of detecting activity other than low fast frequency activity; and 2) provides for a more accurate classification of qualified low fast frequency half waves. These properties 1) and 2) may increase the specificity (lower false positive detections) and sensitivity (lower false negative detections) and possibly improve detection timing (earlier detections), for the particular pattern, e.g., low fast frequency, detection being detected by the detection tool. Such an improvement in event detection provides improved responsive stimulation and thus overall improved patient therapy.

In the example of FIG. 10C, and with reference to the y-axis of FIG. 10C, the range of possible amplitudes is +/−512 units of amplitude. Within this range, the range of values for the negative slope minimum half wave amplitude parameter may be between 0 units and 1022 units, and the range of values for the negative slope maximum half wave amplitude parameter may be between 1 units and 1023 units, with the restriction that the minimum half wave amplitude parameter is always lower than the maximum half wave amplitude parameter. The range of values for the negative slope minimum half wave duration parameter may be between 0 ms (corresponding to 125 Hz for a sampling rate of 250 Hz) and 386 ms (corresponding to approximately 1 Hz for a sampling rate of 250 Hz). The range of values for the negative slope maximum half wave duration parameter may be between 4 ms (corresponding to 62.5 Hz for a sampling rate of 250 Hz) and 400 ms (corresponding to approximately 1 Hz for a sampling rate of 250 Hz).

With respect to positive slope half waves, the range of values for the positive slope minimum half wave amplitude parameter may be between 0 units and 1022 units, and the range of values for the positive slope maximum half wave amplitude parameter may be between 1 units and 1023 units. The range of values for the positive slope minimum half wave duration parameter may be between 0 ms (corresponding to 125 Hz for a sampling rate of 250 Hz) and 386 ms (corresponding to approximately 1 Hz for a sampling rate of 250 Hz). The range of values for the positive slope maximum half wave duration parameter may be between 4 ms (corresponding to 62.5 Hz for a sampling rate of 250 Hz) and 400 ms (corresponding to approximately 1 Hz for a sampling rate of 250 Hz).

Referring again to FIG. 10C, there are eleven half waves in the waveform 1000, namely, a first half wave 1050, the second half wave 1040 (first shown in FIG. 10B), the third half wave 1042 (first shown in FIG. 10B), a fourth half wave 1052, a fifth half wave 1054, a sixth half wave 1056, a seventh half wave 1058, an eighth half wave 1060, a ninth half wave 1062, a tenth half wave 1064, and an eleventh half wave 1066.

A detector can be implemented to target a very specific pattern like the one form by the eighth half wave and the ninth half wave. If the negative slope minimum half wave amplitude parameter is set at a value of 150 units, the negative slope maximum half wave amplitude parameter is set at a value of 250 units, the negative slope minimum half wave duration parameter is set at a value of 0 ms, and the negative slope maximum half wave duration parameter is set at a value of 8 ms; and the positive slope minimum half wave amplitude parameter is set at a value of 300 units, the positive slope maximum half wave amplitude parameter is set at a value of 400 units, the positive slope minimum half wave duration parameter is set at a value of 0 ms, and the positive slope maximum half wave duration parameter is set at a value of 16 ms, for positive slope half waves, then with reference to Table 3 below, only two of the eleven half waves in the waveform segment 1068 will constitute "qualified half waves," namely, the eighth half wave 1060 and the ninth half wave 1062. That is, only one of the five negative slope half waves fall within the amplitude interval defined by the negative slope minimum half wave amplitude parameter and the negative slope maximum half wave amplitude parameter, and the duration interval defined by the negative slope minimum half wave duration parameter and the negative slope maximum half wave duration parameter, and only one of the six positive slope half waves fall within the amplitude interval defined by the positive slope minimum half wave amplitude parameter and the positive slope maximum half wave amplitude parameter, and the duration interval defined by the positive slope minimum half wave duration parameter and the positive slope maximum half wave duration parameter.

Figure 11:
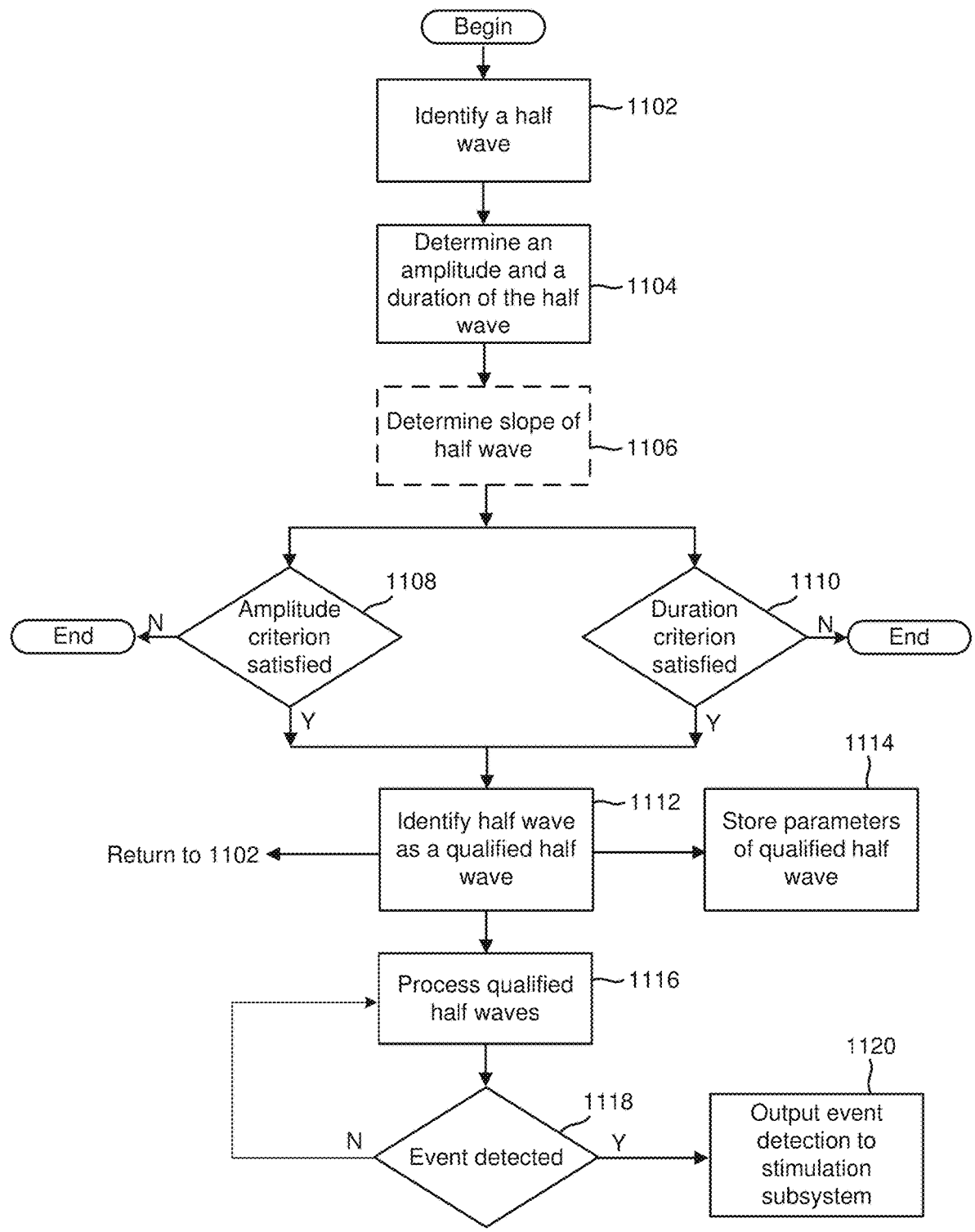
FIG. 11 is a flow chart of a process of detecting an electrical signal of interest from a patient's brain.

FIG. 11 illustrates a method of processing an electrical signal detected from a patient's brain to detect an aspect of the electrical signal that may be used to detect a neurological event. The electrical signal detected from the patient's brain may be an EEG or ECoG, and the aspect may be a qualified half wave. The method may further involve delivery of a therapy in response to detection of a neurological event. The method may be performed by a neurostimulator 110, includ-

TABLE 3

| | $1^{st}$ HW 1050 | $2^{nd}$ HW 1040 | $3^{rd}$ HW 1042 | $4^{th}$ HW 1052 | $5^{th}$ HW 1054 | $6^{th}$ HW 1056 | $7^{th}$ HW 1058 | $8^{th}$ HW 1060 | $9^{th}$ HW 1062 | $10^{th}$ HW 1064 | $11^{th}$ HW 1066 |
|---|---|---|---|---|---|---|---|---|---|---|---|
| Positive or Negative Slope? | Positive | Negative | Positive | Negative | Positive | Negative | Positive | Negative | Positive | Negative | Positive |
| Positive Slope Parameters | | | | | | | | | | | |
| HW Amp. between Min. HW Amp. (300 units) and Max. HW Amp. (400 units) | No | X | No | X | No | X | No | X | Yes | X | No |
| HW Duration between Min. HW Duration (0 ms) and Max. HW Duration (16 ms)? | No | X | No | X | No | X | Yes | X | Yes | X | Yes |
| Negative Slope Parameters | | | | | | | | | | | |
| HW Amp. between Min. HW Amp. (150 units) and Max. HW Amp. (250 units) | X | Yes | X | Yes | X | No | X | Yes | X | Yes | X |
| HW Duration between Min. HW Duration (0 ms) and Max. HW Duration (8 ms)? | X | No | X | No | X | Yes | X | Yes | X | Yes | X |
| Qualified HW? | No | No | No | No | No | No | No | Yes | Yes | No | No |

As mentioned above, the eight-parameter implementation of the half wave detection tool allows the half wave detection tool to detect qualified half waves corresponding to specific low fast frequency activity patterns, while avoiding detection of high amplitude fast frequency activity. This may improve the accuracy of detections of a particular pattern, e.g., low fast frequency. The foregoing may be applicable to other types of activity patterns, such as, for example gamma activity and spike activity. The parameters of the half wave detection tool may be tuned to different values depending on the activity desired to be detected. Examples of neurological event detections based on other types of activity patterns are provided below with reference to FIGS. 14A, 14B, 15, and 16.

Because the detections of qualified have waves are input to a neurological event detection tool, the improved accuracy of qualified half wave detections provided by the four-parameter half wave detection tool may improve the specificity and sensitivity of neurological event detections by the neurological event detection tool. A more specific and sensitive neurological event detection tool provides an improved implantable medical device that reduces both false positive detections of neurological events and false negatives. The additional parameters do not much impact the computational complexity or power consumption of the neurological event detection tool because the extra computational steps resulting from the additional parameters are minimal and do not consume much more than existing neurological event detection tools.

ing for example, a detection subsystem 422 of the neurostimulator and a stimulation subsystem 424 of the neurostimulator.

At step 1102, the detection subsystem 422 identifies a half wave in an electrical signal sensed from the patient's brain. One method of identifying a half wave is disclosed in U.S. Pat. No. 6,810,285. For example, identifying a half wave may involve identifying the beginning and end of an increasing half wave or a decreasing half wave. For example, the detection subsystem 422 may identify an increasing (or positive slope) half wave with an ending amplitude higher than the starting amplitude, as in the second half wave 1008 of FIG. 10A. To do this, a variable corresponding to half wave time is first initialized to zero; then half wave duration, ending threshold, peak amplitude, and first sample value are all initialized. Specifically, the half wave duration value is set to zero; the peak amplitude and first sample values are set to the amplitude value of the last observed sample; and the ending threshold is set to the last observed sample minus a small preset hysteresis value. The first sample value may correspond to the beginning of the increasing half wave.

After waiting for a measurement of the current EEG sample, the half wave time and half wave duration variables are incremented. If the current EEG sample has an amplitude greater than the peak amplitude, then the amplitude of the half wave is increasing (or continues to increase), and the half wave has not ended yet. Accordingly, the ending threshold is reset to be the current EEG sample's amplitude minus the hysteresis value, and the peak is reset to the current EEG sample's amplitude, and the next sample is awaited. If, on the other hand, the current EEG sample has an amplitude less than the ending threshold, then the hysteresis value has been exceeded, and a local extremum has been identified. Accordingly, the end of the increasing half wave has been reached.

At the conclusion of the increasing half wave, the process continues by initializing wave duration, the ending threshold, the peak amplitude, and the first sample value. Wave duration is set to zero, the ending threshold is set to the last sample value plus the hysteresis value, the peak amplitude and the first sample value are set to the most recent sample value.

After waiting for a measurement of the current EEG sample, the half wave time and half wave duration variables are incremented. If the current EEG sample has an amplitude lower than the peak amplitude, then the amplitude of the half wave is decreasing (or continues to decrease). Accordingly, the ending threshold is reset to be the current EEG sample's amplitude plus the hysteresis value, the peak is reset to the current EEG sample's amplitude, and the next sample is awaited.

If the current EEG sample has an amplitude greater than the ending threshold, then the hysteresis value has been exceeded, and a local extremum has been identified. Accordingly, the end of the decreasing half wave has been reached, and the amplitude and duration of the half wave are calculated. The amplitude is equal to the first sample value minus the peak amplitude, and the duration is equal to the current half wave duration. Otherwise, the next EEG sample is awaited.

At step 1104, the detection subsystem 422 determines an amplitude of the half wave and a duration of the half wave. The amplitude and duration of a half wave are determined based on the time and amplitude values of the sample corresponding to the beginning of the half wave and the time and amplitude values of the sample corresponding to the end of a half wave. Once the beginning and the end of the half wave are determined, the amplitude may be calculated as the difference between the amplitude of the sample corresponding to the beginning of the half wave and the amplitude of the sample corresponding to the end of a half wave The duration may be calculated as the difference between the time of the sample corresponding to the beginning of the half wave and the time of the sample corresponding to the end of a half wave.

At step 1106, the detection subsystem 422 may optionally determine if the identified half wave has a positive slope or a negative slope. For example, the waveform morphology analysis unit 712 may determine the direction of the slope in the case of an eight parameter implementation of a half wave detection tool. The direction of slope may be determined based on the amplitude values of adjacent signal samples. When the amplitude values of adjacent signal samples are increasing, the slope is a positive slope. When amplitude values of adjacent signal samples are decreasing, the slope is a negative slope.

At step 1108, the detection subsystem 422 determines if the amplitude satisfies a half wave amplitude criterion defined by a set of amplitude parameters comprising a minimum half wave amplitude and a maximum half wave amplitude. In the case of a four parameter implementation of the half wave detection tool, the half wave amplitude criterion may be considered satisfied when the amplitude of the half wave is between the minimum half wave amplitude and the maximum half wave amplitude. In the case of an eight parameter implementation of the half wave detection tool, a first half wave amplitude criterion for positive-slope half waves is defined by a first set of minimum and maximum amplitude parameters, and a second half wave amplitude criterion for negative-slope half waves is defined by a second set of minimum and maximum amplitude parameters. Each of the first half wave amplitude criterion and the second half wave amplitude criterion may be considered satisfied when the amplitude of the half wave is between the minimum half wave amplitude and the maximum half wave amplitude that defines the criterion.

At step 1110, the detection subsystem 422 determines if the duration satisfies a half wave duration criterion defined by a set of duration parameters comprising a minimum half wave duration and a maximum half wave duration. In the case of a four parameter implementation of the half wave detection tool, the half wave duration criterion may be considered satisfied when the duration of the half wave is between the minimum half wave duration and the maximum half wave duration. In the case of an eight parameter implementation of the half wave detection tool, a first half wave duration criterion for positive-slope half waves is defined by a first set of minimum and maximum duration parameters, and a second half wave duration criterion for negative-slope half waves is defined by a second set of minimum and maximum duration parameters. Each of the first half wave duration criterion and the second half wave duration criterion may be considered satisfied when the duration of the half wave is between the minimum half wave duration and the maximum half wave duration that defines the criterion.

At step 1112, the detection subsystem 422 identifiers the half wave as a qualified half wave when the half wave amplitude criterion is satisfied and the half wave duration criterion is satisfied. In an alternative configuration, the detection subsystem 422 may implement full wave qualification wherein two consecutive half waves, i.e., a full wave, have to be qualified half waves in order for each of the half waves to be qualified. At step 1114, the detection subsystem 422 may store parameters corresponding to qualified half waves, including their directions, slopes, durations, amplitudes, and the elapsed time between adjacent qualified half waves (i.e. the half wave time variable).

As half wave detection is an ongoing and continuous process, the procedure of FIG. 11 preferably does not exit, and loops back to step 1102 for continued identification of half waves and continued processing of half waves to identify qualified half waves. The process of FIG. 11 may, however, be suspended from time to time when conditions or device state call for it, e.g. when the device is inactive or when stimulation is being performed. Once suspended in accordance with the invention, the procedure should recommence with the first initialization step 1110.

With continued reference to FIG. 11, at step 1116, the detection subsystem 422 may process the qualified half waves to determine, at step 1118, whether the electrical signal sensed from the patient's brain includes electrographic activity indicative of a neurological event. To this end, the detection subsystem 422 may maintain a count of the number of qualified half waves occurring within a time window and compare the count to a half wave count criterion. At step 1118, if the count exceeds the half wave count criterion the detection subsystem, at step 1120, outputs an event detection 838 to a stimulation subsystem 424. If the count does not exceed the half wave count criterion at step 1118, the process returns to step 1116, where the detection subsystem 422 continues to process qualified half waves.

The processing of the detection subsystem 422 related to event detection at step 1116 may occur in parallel with processing related to qualified half wave identification. For example, each time a qualified half wave is identified at step 1112, the detection subsystem 422 may, at step 1116, increment a counter. If the count exceeds the half wave criterion within the time window, an event is considered to be detected.

At step 1120, the stimulation subsystem 424 may receive the event detection from the detection subsystem 422 and output an electrical stimulation to the one or more electrodes 412, 414, 416, 418 in response to the event detection.

In the disclosed embodiment of the invention, to reduce power consumption, this procedure is performed in custom electronic hardware; it should be clear that the operations of FIG. 11 are performed in parallel for each active instance of the wave morphology analysis units 712 (FIG. 7). It should also be noted, however, that certain software can also be used to advantageous effect in this context.

Figure 12A:
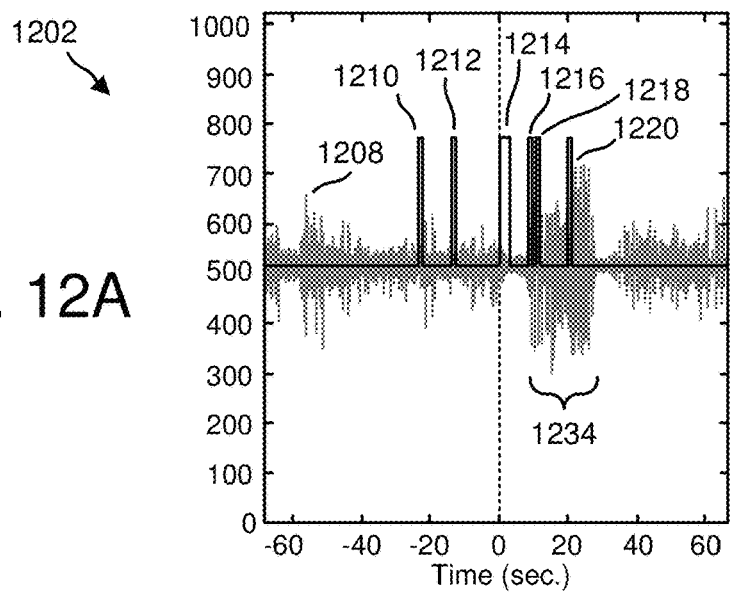
FIGS. 12A, 12B, and 12C are graphical illustrations of an EEG and corresponding seizure-output detections of a first low-fast seizure onset using different configurations of a half wave detection tool.
Figure 12B:
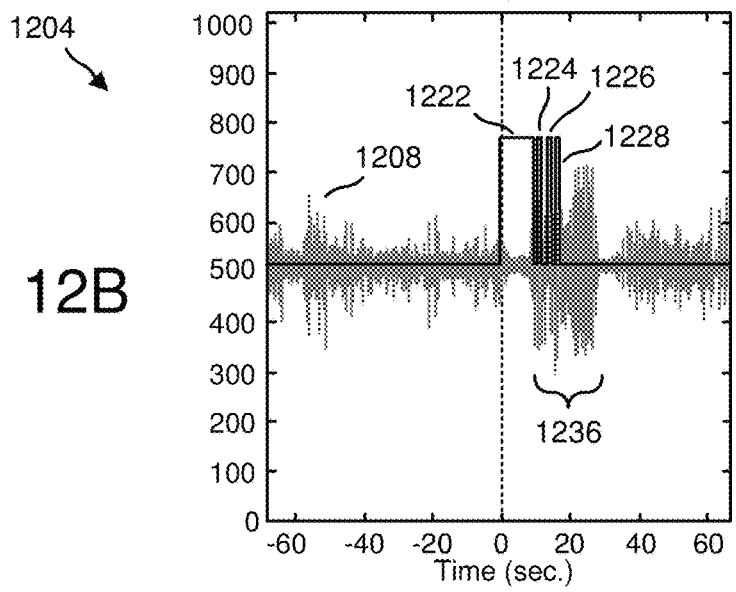
Figure 12C:
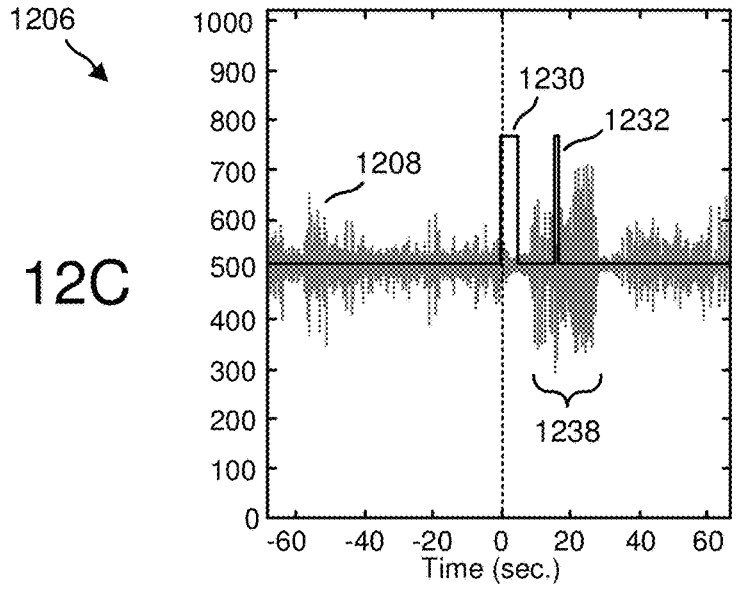

Comparison Between Two Parameter, Four Parameter and Eight Parameter Configurations:

Detecting Low-Fast Seizure Onset:

FIGS. 12A, 12B, and 12C are graphical illustrations 1202, 1204, 1206 of the same EEG 1208 and corresponding seizure-output detections of a first low-fast seizure onset. The graph 1202 in FIG. 12A illustrates the EEG 1208 and a seizure-output detections 1210-1220 resulting from processing of the EEG using a two-parameter configuration of a qualified half wave detection tool. The graph 1204 in FIG. 12B illustrates the EEG 1208 and seizure-output detections 1222-1228 resulting from processing of the EEG using a four-parameter configuration of the qualified half wave detection tool. The graph 1206 in FIG. 12C illustrates the EEG 1208 and seizure-output detections 1230, 1232 resulting from processing of the EEG using an eight-parameter configuration of the qualified half wave detection tool.

Figure 13A:
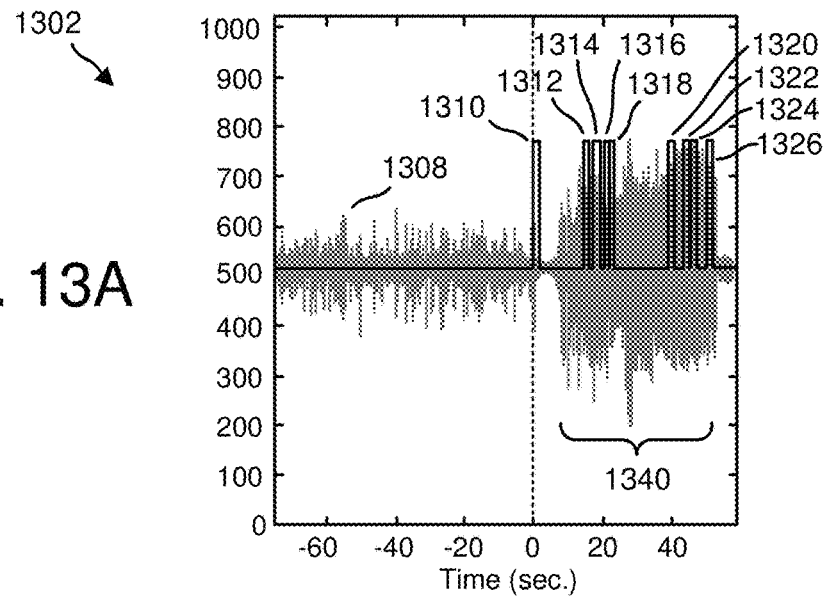
FIGS. 13A, 13B, and 13C are graphical illustrations of an EEG and corresponding seizure-output detections of a second low-fast seizure onset using different configurations of a half wave detection tool.
Figure 13B:
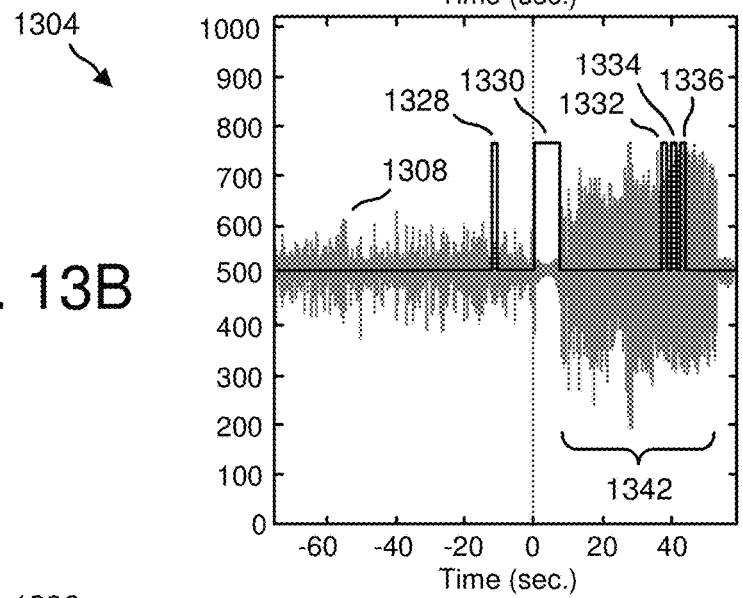
Figure 13C:
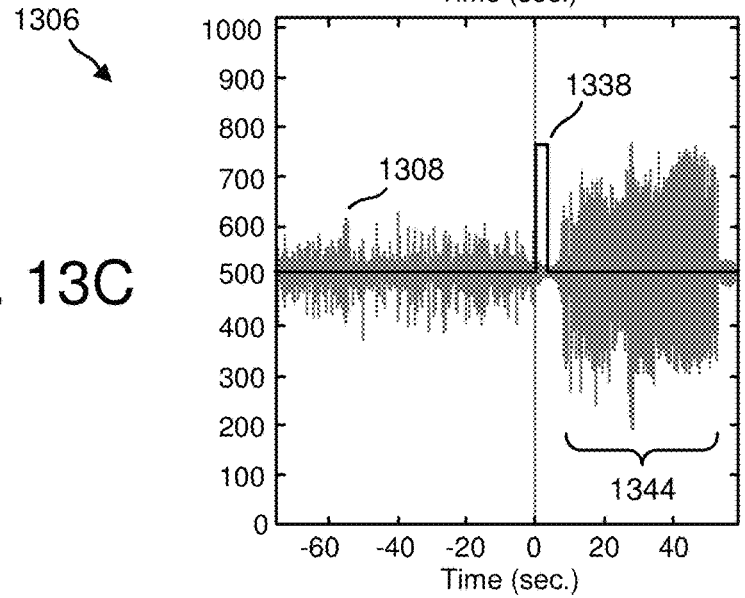

FIGS. 13A, 13B, and 13C are graphical illustrations 1302, 1304, 1306 of the same EEG 1308 and corresponding seizure-output detections of a second low-fast seizure onset. The graph 1302 in FIG. 13A illustrates the EEG 1308 and seizure-output detections 1310-1326 resulting from processing of the EEG using a two-parameter configuration of a qualified half wave detection tool. The graph 1304 in FIG. 13B illustrates the EEG 1308 and seizure-output detections 1328-1336 resulting from processing of the EEG using a four-parameter configuration of the qualified half wave detection tool. The graph 1306 in FIG. 13C illustrates the EEG 1308 and seizure-output detection 1338 resulting from processing of the EEG using an eight-parameter configuration of the qualified half wave detection tool.

The two-parameter configuration of the qualified half wave detection tool includes the following programmed parameters:

[minHWDur 0 ms], and
[minHWAmp 16 units],

The four-parameter configuration of the qualified half wave detection tool includes the following programmed parameters:

[minHWDur 0 ms, maxHWDur 32 ms], and
[minHWAmp 16 units, maxHWAmp 100 units],

The eight-parameter configuration of the qualified half wave detection tool includes the following programmed parameters:

Negative slope:
[minHWDur1 4 ms, maxHWDur1 32 ms], and
[minHWAmp1 40 units, maxHWAmp1 100 units], Positive slope:
[minHWDur2 0 ms, maxHWDur2 12 ms], and
[minHWAmp2 16 units, maxHWAmp2 64 units].

FIGS. 12A, 12B, and 12C each illustrate the same EEG 1208 having an electrographic seizure onset that coincides with the time 0 seconds followed by an electrographic seizure 1234, 1236, 1238. The goal of the above described qualified half wave detection tools is to detect electrographic activity occurring at the time of electrographic seizure onset, i.e., at time 0 seconds, or preferably, slightly prior to the time of electrographic seizure onset. In each EEG 1208, the electrographic seizure begins at onset time 0 seconds and continues for approximately 28 seconds. A detection by the half wave detection tool (represented by the spikes 1210-1232) corresponds to a seizure detection. Depending on the time of the seizure detection, it will be a late onset detection, e.g., detections 1216, 1218, 1220, 1224, 1226, 1228, and 1232, a perfect onset detection at 0 seconds, e.g., detections 1214, 1222, and 1230 or early onset detection, e.g., detections 1210 and 1212, if the detection is a few seconds prior to time 0.

Note that late seizure detections following a perfect onset detection at 0 sec may be expected because EEG patterns similar to the onset pattern at 0 seconds sometimes repeat later as the seizure evolves. These late detections, however, are not the onset. These late detections may be considered part of the seizure evolution as they occur before the seizure ends. For example, with reference to FIG. 12B, the late activities detected at 1224, 1226, and 1228 are patterns very similar to the onset pattern detected at 1222, These late detections 1224, 1226, and 1228 occur during the seizure 1236 and are thus considered part of the seizure evolution.

With reference to FIG. 12A, the two-parameter configuration of a qualified half wave detection tool processed the EEG 1208 and captured: 1) two early seizure onset detections, 1210, 1212, prior to the electrographic seizure onset at time 0 seconds, 2) a perfect seizure onset detection 1214 coincident with the electrographic seizure onset at time 0 seconds, and 3) three late seizure onset detections 1216, 1218, and 1220 after the electrographic seizure onset at time 0 seconds.

With reference to FIG. 12B, the four-parameter configuration of a qualified half wave detection tool captured an initial seizure onset detection 1222 coincident with the electrographic seizure onset at time 0 seconds. The four-parameter configuration of a qualified half wave detection tool also captured three late seizure onset detections 1224, 1226, and 1228, after the electrographic seizure onset at time 0 seconds. Note that the late detections 1224, 1226, 1228 following the initial detection 1222 at 0 seconds are expected because electrographic signals patterns similar to the electrographic signals pattern that resulted in the initial seizure onset detection 1222 at 0 seconds sometimes repeat later as the seizure evolves. The electrographic signals patterns detected by the half wave detection tool at detections 1224, 1226, and 1228 are patterns very similar to the onset pattern detected by the half wave detection tool at the initial detection 1222, but these late detections do not correspond to the seizure onset. The electrographic signals patterns detected by the half wave detection tool at detections 1224, 1226, and 1228 are, however, part of the seizure evolution, as they occur during the 28 seconds duration of the seizure 1236.

With reference to FIG. 12C, the eight-parameter configuration of a qualified half wave detection tool captured an initial seizure onset detection 1230 coincident with the electrographic seizure onset at time 0 seconds. The eight-parameter configuration of a qualified half wave detection tool also captured a late seizure onset detection 1232 after the electrographic seizure onset at time 0 seconds. As described above with reference to FIG. 12B, the late detection 1232 following the initial detection 1230 at 0 seconds is expected because electrographic signals patterns similar to the electrographic signals pattern that resulted in the initial seizure onset detection 1230 at 0 seconds sometimes repeat later as the seizure evolves. The electrographic signals patterns detected by the half wave detection tool at detection 1232 is part of the seizure evolution, as it occur during the 28 seconds duration of the seizure 1238.

From the foregoing graphs, it is noted that onset detections 1214, 1222, 1230 of the low-fast pattern coincident with the electrographic seizure onset at time 0 seconds were obtained with each of the two-parameter configuration of a qualified half wave detection tool (FIG. 12A), the four-parameter configuration of a qualified half wave detection tool (FIG. 12B), and the eight-parameter configuration of a qualified half wave detection (FIG. 12C). The two-parameter configuration of a qualified half wave detection tool (FIG. 12A), however, included two early seizure onset detections 1210, 1212, and three late seizure onset detections 1216, 1218, 1220, while the four-parameter configuration of a qualified half wave detection tool (FIG. 12B) included only three late seizure onset detections 1224, 1226, 1228, and the eight-parameter configuration of a qualified half wave detection (FIG. 12C) included only one late seizure onset detection 1232.

Considering the relative number of additional seizure onset detections (either "early" or "late") output by the respective configurations of the qualified half wave detection tool, it is noted that the performance, e.g., the specificity, of the detection tools improves as the number of parameters increases. Specifically, the two-parameter configuration of a qualified half wave detection tool (FIG. 12A) is the least specific in that it detected five additional seizure onset detections, while the eight-parameter configuration of a qualified half wave detection (FIG. 12C) is most specific in that it detected only one additional seizure onset detection. The specificity of the four-parameter configuration of a qualified half wave detection tool (FIG. 12B) falls between that of the two-parameter and eight-parameter half wave detection tools.

FIGS. 13A, 13B, and 13C each illustrate the same EEG 1308 having an electrographic seizure onset that coincides with the time 0 seconds followed by an electrographic seizure 1340, 1342, 1344. As mentioned above, the goal of the above described qualified half wave detection tools is to detect electrographic activity occurring at the time of electrographic seizure onset, i.e., at time 0 seconds, or preferably, slightly prior to the time of electrographic seizure onset. In each EEG 1308, the electrographic seizure onset begins at time 0 seconds and continues for approximately 50 seconds. A detection by the half wave detection tool (represented by the spikes 1310-1338) between −10 and 50 seconds corresponds to a seizure detection. Depending on the time of the seizure detection, it will be a late onset detection, e.g., detections 1312, 1314, 1316, 1318, 1320, 1322, 1324, 1326, 1332, 1334, and 1336, a perfect onset detection at 0 seconds, e.g., detections 1310, 1330, and 1338, or early onset detection, e.g., 1328, if it is a few seconds prior to time 0.

With reference to FIG. 13A, the two-parameter configuration of a qualified half wave detection tool processed the EEG 1308 and captured an initial seizure onset detection 1310 coincident with the electrographic seizure onset at time 0 seconds. The two-parameter configuration of a qualified half wave detection tool also captured eight late seizure onset detections 1312-1326, after the electrographic seizure onset at time 0 seconds. As noted above, the additional late detections 1312-1326 following the initial detection 1310 are expected because electrographic signals patterns similar to the electrographic signals pattern that resulted in the initial seizure onset detection 1310 repeat later as the seizure evolves. The electrographic signals patterns detected by the half wave detection tool at detections 1312-1326 are patterns very similar to the onset pattern detected by the half wave detection tool at the initial late detection 1310. The electrographic signals patterns detected by the half wave detection tool at detections 1312-1326 are part of the seizure evolution, as they occur during the 50 seconds duration of the seizure 1340.

With reference to FIG. 13B, the four-parameter configuration of a qualified half wave detection tool captured an initial seizure onset detection 1330 coincident with the electrographic seizure onset at time 0 seconds. The four-parameter configuration of a qualified half wave detection tool also captured three late seizure onset detections 1332, 1334, 1336, after the electrographic seizure onset at time 0 seconds. Note that the late detections 1332, 1334, 1336 following the initial detection 1330 at 0 seconds are expected because electrographic signals patterns similar to the electrographic signals pattern that resulted in the initial seizure onset detection 1330 at 0 seconds sometimes repeat later as the seizure evolves. The electrographic signals patterns detected by the half wave detection tool at detections 1332, 1334, and 1336 are patterns very similar to the onset pattern detected by the half wave detection tool at the initial detection 1330, but these late detections do not correspond to the seizure onset. The electrographic signals patterns detected by the half wave detection tool at detections 1332, 1334, and 1336 are, however, part of the seizure evolution, as they occur during the 50 seconds duration of the seizure 1242. The four-parameter configuration of a qualified half wave detection tool also captured an early seizure onset detection 1328, at approximately −15 seconds before the electrographic seizure onset at time 0 seconds. The early seizure onset detection 1328 may be considered a false positive detection for the seizure onset at time 0 seconds. The electrographic activity pattern corresponding to the early seizure onset detection 1328, however, resembles the electrographic activity pattern corresponding to the actual seizure onset at time 0, and may be considered a precursor to an actual seizure, Thus, an early seizure onset detection 1328 is acceptable and in some cases desirable. For example, since the early seizure onset detection 1328 is captured a few seconds before the actual seizure onset at time 0 seconds, responsive stimulation therapy may be initiated ahead of the actual seizure to thereby possibly prevent the seizure from occurring or reduce the severity of the seizure.

With reference to FIG. 13C, the eight-parameter configuration of a qualified half wave detection tool captured an initial seizure onset detection 1338 coincident with the electrographic seizure onset at time 0 seconds. The eight-parameter configuration of a qualified half wave detection tool did not capture any early seizure onset detections prior to the electrographic seizure onset at time 0 seconds, or any late seizure onset detections after the electrographic seizure onset at time 0 seconds.

From the foregoing graphs, it is noted that onset detections 1310, 1330, 1338 of the low-fast pattern coincident with the electrographic seizure onset at time 0 seconds were obtained with each of the two-parameter configuration of a qualified half wave detection tool (FIG. 13A), the four-parameter configuration of a qualified half wave detection tool (FIG. 13B), and the eight-parameter configuration of a qualified half wave detection (FIG. 13C). The two-parameter configuration of a qualified half wave detection tool (FIG. 13A), however, included eight late seizure onset detections 1312-1326, while the four-parameter configuration of a qualified half wave detection tool (FIG. 13B) included only three late seizure onset detections 1332, 1334, 1336, and the eight-parameter configuration of a qualified half wave detection (FIG. 13C) included no late seizure onset detections.

Considering the relative number of additional seizure onset detections (either "early" or "late") output by the respective configurations of the qualified half wave detection tool, it is noted once again that the performance, e.g., the specificity, of the detection tools improves as the number of parameters increases. Specifically, the two-parameter configuration of a qualified half wave detection tool (FIG. 13A) is the least specific in that it detected eight additional seizure onset detections, while the eight-parameter configuration of a qualified half wave detection (FIG. 13C) is the most specific in that it detected no additional seizure onset detection. The specificity of the four-parameter configuration of a qualified half wave detection tool (FIG. 13B) falls between that of the two-parameter and eight-parameter half wave detection tools.

Figure 14A:
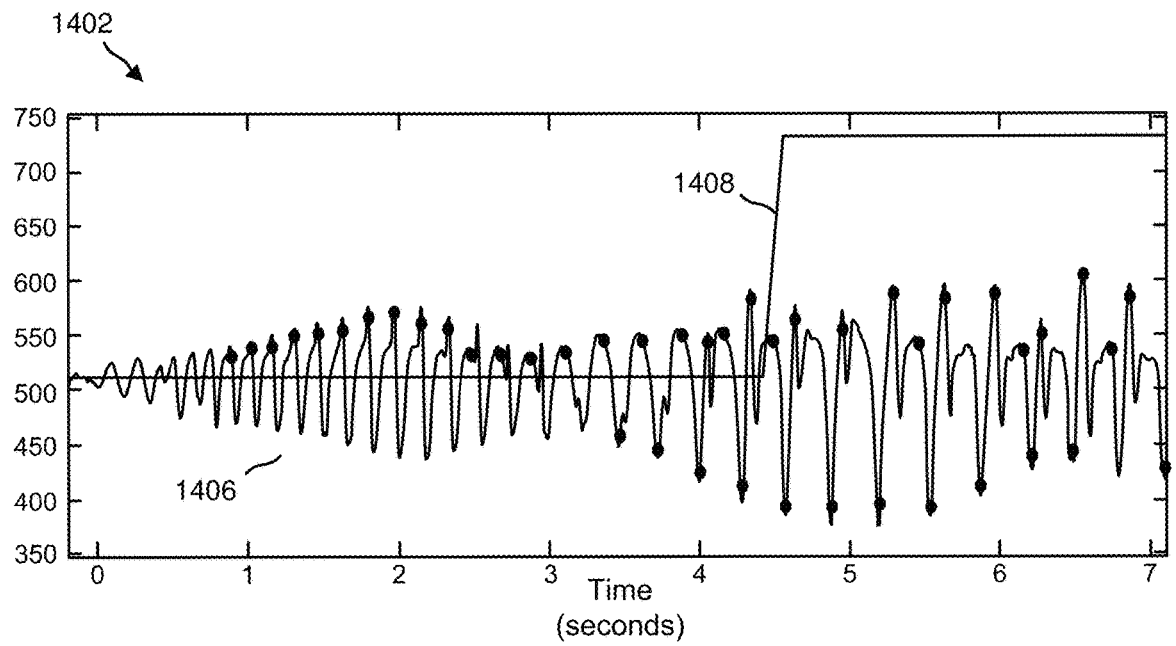
FIGS. 14A and 14B are graphical illustrations of an EEG and detections of theta frequency activity using different configurations of a half wave detection tool.
Figure 14B:
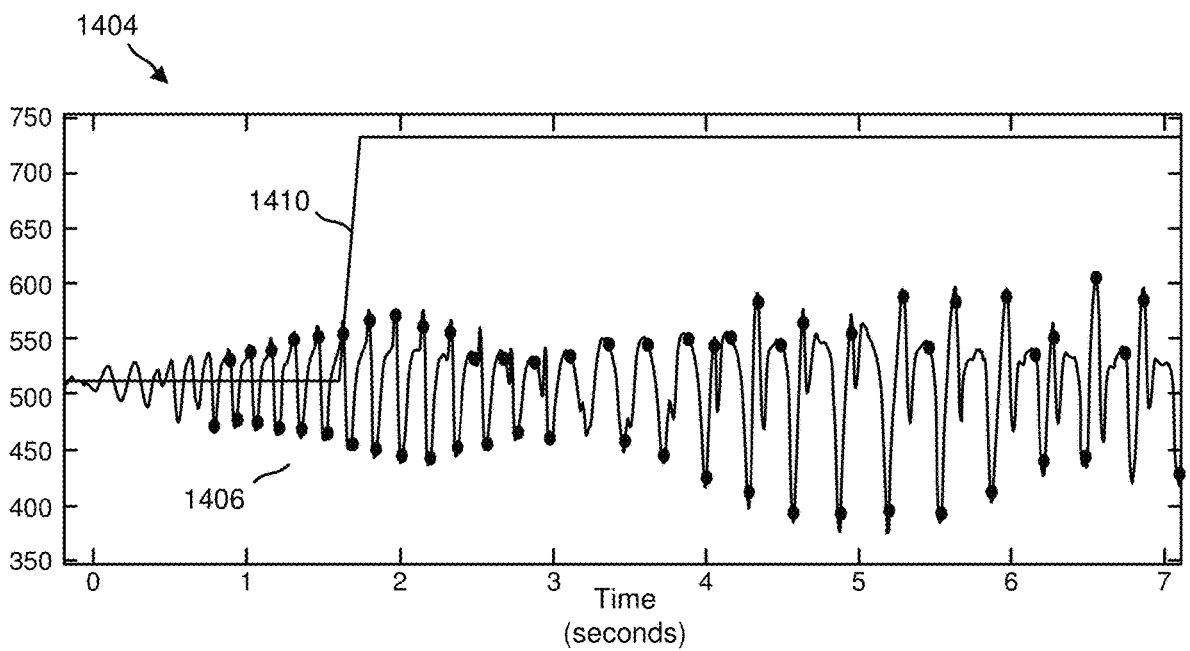

Comparison Between Four Parameter and Eight Parameter Configurations:

Detecting Theta Frequency Activity:

FIGS. 14A and 14B are graphical illustrations 1402, 1404 of the same EEG 1406 and corresponding detections of theta frequency activity. The graph 1402 in FIG. 14A illustrates the EEG 1406 and a detection 1408 resulting from processing of the EEG using a four-parameter configuration of a qualified half wave detection tool. The graph 1404 in FIG. 14B illustrates the EEG 1406 and a detection 1410 resulting from processing of the EEG using an eight-parameter configuration of the qualified half wave detection tool. In both of FIG. 14A and FIG. 14B, the solid dots represent qualified half wave detections.

The four-parameter configuration of the qualified half wave detection tool includes the following programmed parameters:

[minHWDur 13 ms, maxHWDur 50 ms], and
[minHWAmp 64 units, maxHWAmp 900 units],

The eight-parameter configuration of the qualified half wave detection tool includes the following programmed parameters:

Negative slope:
[minHWDur1 1 ms, maxHWDur 1 50 ms], and
[minHWAmp1 64 units, maxHWAmp1 900 units],
Positive slope:
[minHWDur2 13 ms, maxHWDur2 50 ms], and
[minHWAmp2 64 units, maxHWAmp2 900 units].

In one configuration, the eight-parameter configuration of the qualified half wave detection tool may further require detection of consecutive half waves in order to consider a half wave to be a qualified half wave.

From FIGS. 14A and 14B it is noted that the detection 1410 output by the eight-parameter version of the half wave detection tool occurs approximately 2.75 seconds earlier than the detection 1408 output by the four-parameter version of the half wave detection tool. Thus, in this example, the eight-parameter version of the half wave detection tool may be considered to be more specific than the four-parameter version of the half wave detection tool in that its onset detection is more timely. If the range of the half wave duration parameter minHWDur for the four-parameter version of the half wave detection tool is changed to 1 ms, it can detect the onset as good as the eight-parameter configuration of the half wave tool but very likely there will be more detections during baseline periods because the detector is less specific.

Figure 15:
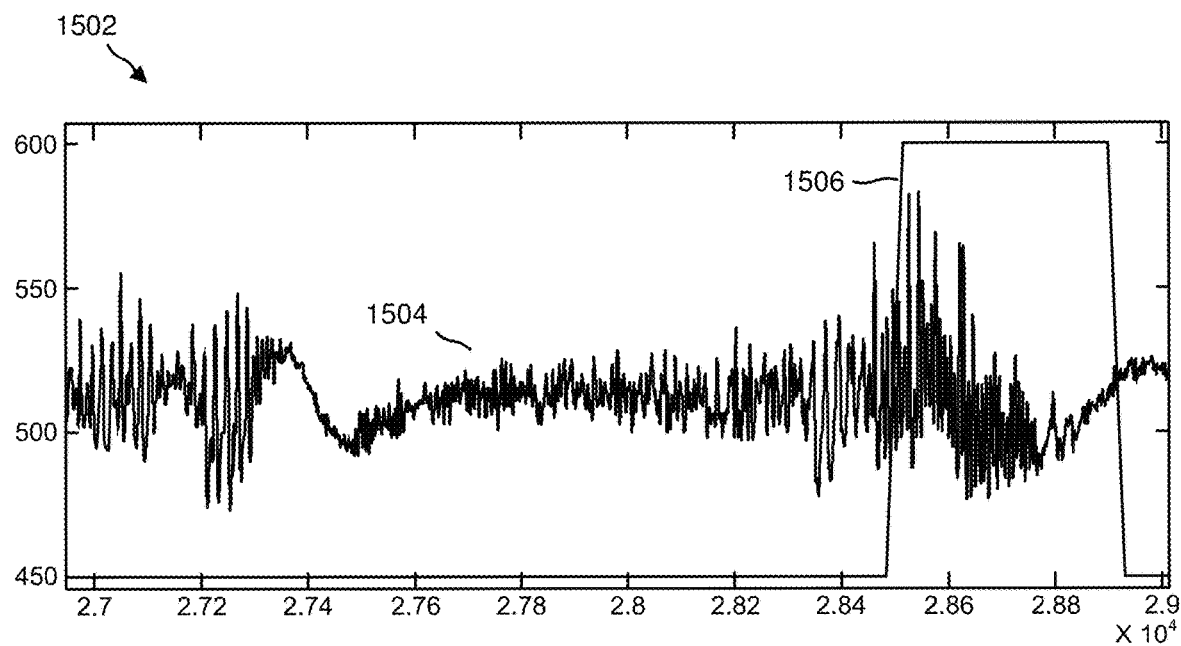
FIG. 15 is a graphical illustration of an EEG and a detection of a gamma activity using a half wave detection tool.

Additional Examples of Four-Parameter Half Wave Detection Tools:

Gamma Detector:

FIG. 15 is a graphical illustration 1502 of an EEG 1504 and a detection 1506 of a gamma activity, wherein the half wave detection tool is tuned or tailored to detect fast activity with increasing high amplitude. The detection 1506 resulted from the processing of the EEG 1504 using a four-parameter configuration of a qualified half wave detection tool. An example four-parameter configuration of the qualified half wave detection tool for detection of gamma activity includes the following programmed parameters:

[minHWDur 0 ms, maxHWDur 12 ms], and
[minHWAmp 24 units, maxHWAmp 200 units].

Figure 16:
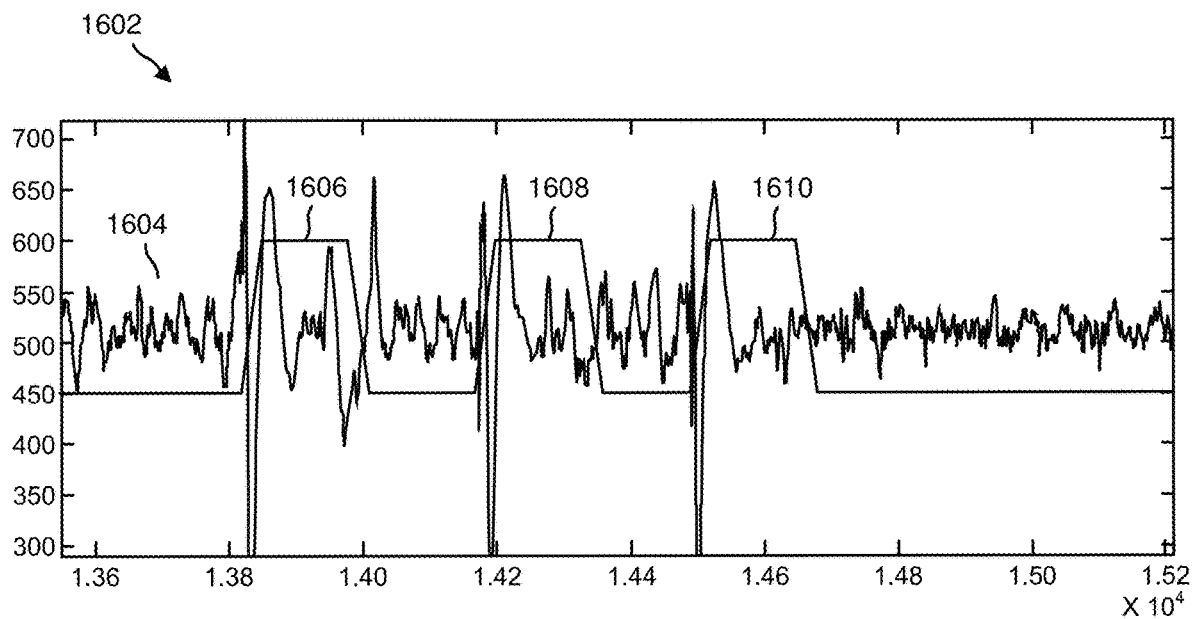
FIG. 16 is a graphical illustration of an EEG and a number of detections of spike activity using a half wave detection tool.

Spike Detector:

FIG. 16 is a graphical illustration 1602 of an EEG 1604 and a number of detections 1606, 1608, 1610 of spike activity. The detections 1606, 1608, 1610 resulted from the processing of the EEG 1604 using a four-parameter configuration of a qualified half wave detection tool. A example four-parameter configuration of the qualified half wave detection tool for detection of spike activity includes the following programmed parameters:

[minHWDur 0 ms, maxHWDur 24 ms], and
[minHWAmp 200 units, maxHWAmp 1023 units].

It should be observed that while the foregoing detailed description of various embodiments of the present invention is set forth in some detail, the invention is not limited to those details and an implantable neurostimulator or neurological disorder detection device made according to the invention can differ from the disclosed embodiments in numerous ways. In particular, it will be appreciated that embodiments of the present invention may be employed in many different applications to detect anomalous neurological characteristics in at least one portion of a patient's brain. It will be appreciated that the functions disclosed herein as being performed by hardware and software, respectively, may be performed differently in an alternative embodiment. It should be further noted that functional distinctions are made above for purposes of explanation and clarity; structural distinctions in a system or method according to the invention may not be drawn along the same boundaries. Hence, the appropriate scope hereof is deemed to be in accordance with the claims as set forth below.

It will be appreciated that the above-disclosed and other features and functions, or alternatives thereof, may be desirably combined into many other different systems or applications. It will also be appreciated that various presently unforeseen or unanticipated alternatives, modifications, variations or improvements therein may be subsequently made by those skilled in the art which are also intended to be encompassed by the following claims.

What is claimed is:

1. An implantable medical device, comprising:
one or more electrodes configured to be implanted on or in a brain; and
a waveform analyzer configured to:
identify a half wave in an electrical signal sensed by the one or more electrodes;
determine an amplitude of the half wave and a duration of the half wave;

determine whether the identified half wave has a positive slope or a negative slope;

in a case of a positive-slope half wave, determine if the amplitude satisfies a positive-slope half wave amplitude criterion defined by a first set of amplitude parameters comprising a minimum amplitude and a maximum amplitude, and if the duration satisfies a positive-slope half wave duration criterion defined by a first set of duration parameters comprising a minimum duration and a maximum duration;

in a case of a negative-slope half wave, determine if the amplitude satisfies a negative-slope half wave amplitude criterion defined by a second set of amplitude parameters comprising a minimum amplitude and a maximum amplitude that is different from the first set of amplitude parameters, and if the duration satisfies a negative-slope half wave duration criterion defined by a second set of duration parameters comprising a minimum duration and a maximum duration that is different from the first set of duration parameters;

identify the half wave as a qualified half wave when each of the half wave amplitude criterion and the half wave duration criterion is satisfied;

determine, based on a count of a number of qualified half waves occurring within a time window and a half wave count criterion, whether the electrical signal includes electrographic activity indicative of epileptiform activity; and output an event detection upon determining the electrical signal includes electrographic activity indicative of epileptiform activity; and a stimulation subsystem coupled to the one or more electrodes and configured to receive the event detection from the waveform analyzer and to output an electrical stimulation to the one or more electrodes in response to the event detection.

2. The implantable medical device of claim 1, wherein the half wave amplitude criterion is satisfied when the amplitude of the half wave is between the minimum half wave amplitude and the maximum half wave amplitude.

3. The implantable medical device of claim 1, wherein the half wave duration criterion is satisfied when the duration of the half wave is between the minimum half wave duration and the maximum half wave duration.

4. The implantable medical device of claim 1, wherein the processor is configured to:

determine the count of the number of qualified half waves occurring within the time window;

compare the count to the half wave count criterion; and determine the electrical signal includes electrographic activity indicative of epileptiform activity when the count exceeds the half wave count criterion.

5. The implantable medical device of claim 1, wherein the epileptiform activity corresponds to one of an epileptic seizure or a seizure onset.

6. The implantable medical device of claim 1, wherein:

the first set of amplitude parameters includes a positive-slope minimum half wave amplitude of between 0 and 1022 units of amplitude, and a positive-slope maximum half wave amplitude of between 1 and 1023 units of amplitude; and the first set of duration parameters includes a positive-slope minimum half wave duration of between 0 and 386 ms, and a positive-slope maximum half wave duration of between 4 and 400 ms.

7. The implantable medical device of claim 1, wherein the second set of amplitude parameters is a negative-slope minimum half wave amplitude of between 0 and 1022 units of amplitude, and a negative-slope maximum half wave amplitude of between 1 and 1023 units of amplitude; and the second set of duration parameters comprises a negative-slope minimum half wave duration of between 0 and 386 ms, and a negative-slope maximum half wave duration of between 4 and 400 ms.

8. A method of an implanted medical device, the method comprising:

identifying a half wave in an electrical signal sensed from a brain;

determining an amplitude of the half wave and a duration of the half wave;

determining whether the identified half wave has a positive slope or a negative slope;

in a case of a positive-slope half wave, determining if the amplitude satisfies a positive-slope half wave amplitude criterion defined by a first set of amplitude parameters comprising a minimum amplitude and a maximum amplitude, and if the duration satisfies a positive-slope half wave duration criterion defined by a first set of duration parameters comprising a minimum duration and a maximum duration;

in a case of a negative-slope half wave, determining if the amplitude satisfies a negative-slope half wave amplitude criterion defined by a second set of amplitude parameters comprising a minimum amplitude and a maximum amplitude that is different from the first set of amplitude parameters, and if the duration satisfies a negative-slope half wave duration criterion defined by a second set of duration parameters comprising a minimum duration and a maximum duration that is different from the first set of duration parameters;

identifying the half wave as a qualified half wave when each of the half wave amplitude criterion and the half wave duration criterion is satisfied; and determining, based on a count of a number of qualified half waves occurring within a time window and a half wave count criterion, whether the electrical signal includes electrographic activity indicative of epileptiform activity;

outputting an electrical stimulation to one or more electrodes upon determining the electrical signal includes electrographic activity indicative of epileptiform activity.

9. The method of claim 8, wherein the half wave amplitude criterion is satisfied when the amplitude of the half wave is between the minimum half wave amplitude and the maximum half wave amplitude.

10. The method of claim 8, wherein the half wave duration criterion is satisfied when the duration of the half wave is between the minimum half wave duration and the maximum half wave duration.

11. The method of claim 8, further comprising:

determining the count of the number of qualified half waves occurring within the time window;

comparing the count to the half wave count criterion; and determining the electrical signal includes electrographic activity indicative of epileptiform activity when the count exceeds the half wave count criterion.

12. The method of claim 8, wherein the epileptiform activity corresponds to one of an epileptic seizure or a seizure onset.

13. The method of claim 8, wherein:
the first set of amplitude parameters includes a positive-slope minimum half wave amplitude of between 0 and 1022 units of amplitude, and a positive-slope maximum half wave amplitude of between 1 and 1023 units of amplitude; and
the first set of duration parameters includes a positive-slope minimum half wave duration of between 0 and 386 ms, and a positive-slope maximum half wave duration of between 4 and 400 ms.

14. The method of claim 8, wherein
the second set of amplitude parameters is a negative-slope minimum half wave amplitude of between 0 and 1022 units of amplitude, and a negative-slope maximum half wave amplitude of between 1 and 1023 units of amplitude; and
the second set of duration parameters comprises a negative-slope minimum half wave duration of between 0 and 386 ms, and a negative-slope maximum half wave duration of between 4 and 400 ms.

* * * * *